(12) United States Patent
Ottoboni et al.

(10) Patent No.: US 11,878,074 B2
(45) Date of Patent: *Jan. 23, 2024

(54) METHODS OF USE OF EMULSION FORMULATIONS OF AN NK-1 RECEPTOR ANTAGONIST

(71) Applicant: Heron Therapeutics, Inc., San Diego, CA (US)

(72) Inventors: Thomas B. Ottoboni, Belmont, CA (US); Han Han, Sunnyvale, CA (US)

(73) Assignee: Heron Therapeutics, Inc., San Diego, CA (US)

( * ) Notice: Subject to any disclaimer, the term of this patent is extended or adjusted under 35 U.S.C. 154(b) by 380 days.

This patent is subject to a terminal disclaimer.

(21) Appl. No.: 17/180,593

(22) Filed: Feb. 19, 2021

(65) Prior Publication Data

US 2021/0173877 A1 Jun. 10, 2021

Related U.S. Application Data

(63) Continuation of application No. 16/820,311, filed on Mar. 16, 2020, now Pat. No. 11,173,118, which is a continuation of application No. 15/965,638, filed on Apr. 27, 2018, now Pat. No. 10,624,850, which is a continuation of application No. 15/012,532, filed on Feb. 1, 2016, now Pat. No. 9,974,742.

(51) Int. Cl.
| | |
|---|---|
| *A61K 9/107* | (2006.01) |
| *A61K 9/00* | (2006.01) |
| *A61K 47/24* | (2006.01) |
| *A61K 47/44* | (2017.01) |
| *A61K 47/10* | (2017.01) |
| *A61K 31/435* | (2006.01) |
| *A61K 31/496* | (2006.01) |
| *A61K 31/43* | (2006.01) |
| *A61K 31/5377* | (2006.01) |
| *A61K 31/573* | (2006.01) |
| *G06F 16/9038* | (2019.01) |
| *G06N 20/00* | (2019.01) |
| *G06F 16/903* | (2019.01) |

(52) U.S. Cl.
CPC .......... *A61K 9/1075* (2013.01); *A61K 9/0019* (2013.01); *A61K 31/43* (2013.01); *A61K 31/435* (2013.01); *A61K 31/496* (2013.01); *A61K 31/5377* (2013.01); *A61K 31/573* (2013.01); *A61K 47/10* (2013.01); *A61K 47/24* (2013.01); *A61K 47/44* (2013.01); *G06F 16/9038* (2019.01); *G06F 16/90344* (2019.01); *G06N 20/00* (2019.01)

(58) Field of Classification Search
CPC .... A61K 9/1075; A61K 9/0019; A61K 31/43; A61K 31/435; A61K 31/496; A61K 31/5377; A61K 31/573; A61K 47/10; A61K 47/24; A61K 47/44; G06F 16/9038; G06F 16/90344; G06N 20/00

See application file for complete search history.

(56) References Cited

U.S. PATENT DOCUMENTS

| | | | |
|---|---|---|---|
| 5,616,330 A | 4/1997 | Kaufman et al. | |
| 9,561,229 B2 * | 2/2017 | Ottoboni | A61K 47/12 |
| 9,808,465 B2 * | 11/2017 | Ottoboni | A61K 47/26 |
| 9,974,742 B2 * | 5/2018 | Ottoboni | G06N 20/00 |
| 9,974,793 B2 * | 5/2018 | Ottoboni | A61K 47/26 |
| 9,974,794 B2 | 5/2018 | Ottoboni et al. | |
| 10,500,208 B2 * | 12/2019 | Ottoboni | A61K 9/107 |
| 10,624,850 B2 * | 4/2020 | Ottoboni | A61K 31/496 |
| 10,953,018 B2 * | 3/2021 | Ottoboni | A61K 31/5377 |
| 11,173,118 B2 * | 11/2021 | Ottoboni | A61K 47/24 |
| 2007/0071777 A1 | 3/2007 | Bromer et al. | |
| 2011/0009362 A1 | 1/2011 | Joshi et al. | |
| 2011/0038925 A1 | 2/2011 | Wan | |
| 2013/0236501 A1 | 9/2013 | Booth et al. | |
| 2013/0317016 A1 | 11/2013 | Hingorani et al. | |
| 2016/0024092 A1 | 1/2016 | Wan et al. | |
| 2016/0082013 A1 | 3/2016 | Ottoboni et al. | |
| 2016/0206622 A1 | 3/2016 | Ottoboni et al. | |
| 2017/0112847 A1 | 4/2017 | Ottoboni et al. | |

(Continued)

FOREIGN PATENT DOCUMENTS

| | | | |
|---|---|---|---|
| CN | 102379845 A | * | 3/2012 |
| CN | 102379845 A | | 3/2012 |

(Continued)

OTHER PUBLICATIONS

Applicant initiated interview, Examiners Summary, dated Aug. 31, 2016, for U.S. Appl. No. 15/083,071, now U.S. Pat. No. 9,561,229, 4 pages (2016).

(Continued)

*Primary Examiner* — Brandon J Fetterolf
*Assistant Examiner* — Manahil Mirghani Ali Abdalhameed
(74) *Attorney, Agent, or Firm* — McDermott Will & Emery LLP; Judy M. Mohr; Peter Brunovskis

(57) ABSTRACT

Disclosed herein are novel pharmaceutical formulations of a neurokinin-1 (NK-1) receptor antagonist suitable for parenteral administration including intravenous administration. Also included are formulations including both the NK-1 receptor antagonist and dexamethasone sodium phosphate. The pharmaceutical formulations are stable oil-in-water emulsions for non-oral treatment of emesis and are particularly useful for treatment of subjects undergoing highly emetogenic cancer chemotherapy.

14 Claims, 4 Drawing Sheets

(56) References Cited

U.S. PATENT DOCUMENTS

| | | |
|---|---|---|
| 2017/0216205 A1 | 8/2017 | Ottoboni et al. |
| 2018/0000828 A1 | 1/2018 | Ottoboni et al. |
| 2018/0000829 A1 | 1/2018 | Ottoboni et al. |
| 2019/0000762 A1 | 1/2019 | Ottoboni et al. |
| 2020/0383914 A1 | 12/2020 | Ottoboni et al. |

FOREIGN PATENT DOCUMENTS

| | | | |
|---|---|---|---|
| WO | WO 2005/016308 A1 | 2/2005 | |
| WO | WO 2009/124756 A1 | 10/2009 | |
| WO | WO 2011/158053 A1 | 12/2011 | |
| WO | WO 2013/177501 A2 | 11/2013 | |
| WO | WO 2014/005606 A1 | 1/2014 | |
| WO | WO 2014/209962 A1 | 12/2014 | |
| WO | WO 2016/044784 A1 | 3/2016 | |

OTHER PUBLICATIONS

Aziz, "Neurokinin-1 receptor antagonists for chemotherapy-induced nausea and vomiting", Ann. Palliat. Med., vol. 1, No. 2, pp. 130-136 (2012).

Declaration of Thomas Ottoboni under 37 C.F.R. § 1.132, filed Sep. 1, 2016 in regard to U.S. Appl. No. 15/083,071, now U.S. Pat. No. 9,561,229, 9 pages (2016).

Dexamethasone Hydrogen Phosphate retrieved from the internet from web.archive.org/web/20141224130045/http://www.drugs.com/pro/dexamethasone-sodium-phosphate.html (2017).

Cassileth et al., "Antiemetic efficacy of dexamethasone therapy in patients receiving cancer chemotherapy", Arch. Intern. Med., vol. 143, No. 7, pp. 1347-1349 (1983) Abstract Only.

Curran et al., "Aprepitant: a review of its use in the prevention of nausea and vomiting", Drugs, vol. 69, No. 13, pp. 1853-1878 (2009).

Hargreaves et al., "Development of aprepitant, the first neurokinin-1 receptor antagonist for the prevention of chemotherapy-induced nausea and vomiting", Ann. N.Y. Acad. Sci., vol. 1222, pp. 40-48 (2011).

International Search Report from PCT Patent Application No. PCT/US2015/051050 dated Dec. 18, 2015, Application now published as International Publication No. WO2016/044784 on Mar. 24, 2016.

International Search Report from PCT Patent Application No. PCT/2016/015992 dated Jun. 3, 2016.

Lipoid GmbH, Lipoid Product Finder, Retrieved from the internet http://www.lipiod.com/en/node/105, 1 page (2018).

Lipoid GmbH, Lipoid Product Finder, print friendly version, Retrieved from the internet <URL: http://www.lipoid.com/en/print/105, 2 pages (2018).

Navari et al., "Reduction of cisplatin-induced emesis by a selective neurokinin-1-receptor antagonist. L-754,030 Antiemetic Trials Group", N. Engl. J. Med., vol. 340, No. 3, pp. 190-195 (1999).

Sun et al., "Compatibility of intravenous fosaprepitant with intravenous 5-HT3 antagonists and corticosteroids", Cancer Chemother. Pharmacol., vol. 72, No. 3, pp. 509-513 (2013).

The Pharmaceutics and Compounding Laboratory, "Emulsions: Preparation and Stabilization, Methods of emulsion preparation", 1 page, Online article accessed May 26, 2016 from http://pharmlabs.unc.edu/labs/emulsions/prep.htm.

Zhou et al., "Preparation of Aprepitant emulsion for intravenous injection", Chinese Journal of Pharmaceuticals, vol. 43, No. 12, pp. 1003-1006 (2012) English Translation Only.

\* cited by examiner

METHODS OF USE OF EMULSION FORMULATIONS OF AN NK-1 RECEPTOR ANTAGONIST

CROSS-REFERENCE TO RELATED APPLICATIONS

This application is a continuation of U.S. application Ser. No. 16/820,311, filed Mar. 16, 2020, pending, which is a continuation of U.S. application Ser. No. 15/965,638, filed Apr. 27, 2018, now U.S. Pat. No. 10,624,850, which is a continuation of U.S. application Ser. No. 15/012,532, filed Feb. 1, 2016, now U.S. Pat. No. 9,974,742, each of which is incorporated herein in its entirety.

TECHNICAL FIELD

The disclosure relates generally to emulsion formulations and systems for the intravenous or parenteral administration of an NK-1 receptor antagonist for treatment of emesis. The emulsion formulations are stable for prolonged periods of time. Also described are methods for preparing the stable NK-1 receptor antagonist emulsions and pharmaceutical formulations.

BACKGROUND

Emesis is a critical problem experienced as a result of anticancer cytotoxic therapy. Up to 80% of patients will experience chemotherapy-induced nausea and vomiting (CINV) without prophylactic therapy (Vieira dos Santos et al., 2012, J Natl Cancer Inst, 104:1280-1292). Navari et al. (1999, N Engl J Med, 340:190-195) showed that neurokinin-1 (NK-1) receptor antagonists improve CINV when used in combination with cisplatin-based chemotherapy. NK-1 receptor antagonists block binding of substance P to the receptor, thereby preventing or limiting induction of vomiting pathways mediated by the NK-1 receptor (Aziz, 2012, Ann Palliat Med, 1:130-136).

NK-1 receptor antagonists currently approved and marketed include aprepitant and rolapitant HCl, which are both available in oral form. Not surprisingly, oral dosage forms can create a problem for patients suffering from emesis, specifically, for example, on days two and three of chemotherapy. Accordingly, it is desirable to have injectable formulations to simplify treatment for these patients. Described herein are emulsions formulated for administering to a patient by injection. These emulsions are formulated to contain neurokinin-1 receptor antagonists which may be poorly soluble in aqueous solvents or unstable in aqueous-based liquid formulations.

Liquid formulations containing NK-1 receptor antagonists having poor solubility and/or poor gastrointestinal permeability characteristics can be very challenging to formulate for purposes of long-term storage and for administration. One means of addressing this challenge is to prepare an emulsion which may both allow preparation of an injectable formulation as well as enhance bioavailability of the active agent once administered.

Intravenous emulsions should have a very small droplet size to circulate in the bloodstream without causing capillary blockage and embolization. These size limits are typified by USP33-NF28 General Chapter <729> for Globule Size Distribution in Lipid Injectable Emulsions, hereinafter referred to as USP <729>, which defines universal limits for (1) mean droplet size not exceeding 500 nm or 0.5 µm and (2) the population of large-diameter fat globules, expressed as the volume-weighted percentage of fat greater than 5 µm (PFAT5) not exceeding 0.05%, irrespective of the final lipid concentration.

Emulsion formulations must be physically stable. The droplet size limits defined in USP <729> apply throughout the assigned shelf life. All true emulsions are thermodynamically unstable and may over time undergo a range of processes which tend to increase the droplet size. These include direct droplet coalescence, when two droplets collide and form a single new droplet; and aggregation, in which droplets adhere together to form larger masses. Aggregation may in some cases be a precursor of further coalescence into larger droplets. These processes may result in large aggregates rising to the surface of the container, a phenomenon known as 'creaming', and ultimately to free oil being visible on the emulsion surface, known as 'cracking'.

Emulsion formulations must also be chemically stable. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation. Thus, pH should be controlled during manufacture and parenteral emulsion formulations may include a buffering agent to provide additional control. Any decrease in pH over the assigned shelf-life may be indicative of chemical degradation.

In the present application, emulsion formulations were prepared and characterized to identify a formulation and process that will allow an NK-1 receptor antagonist compound to be incorporated into an emulsion for intravenous injection and remain stable during the shelf life of the formulation.

BRIEF SUMMARY

The following aspects and embodiments thereof described and illustrated below are meant to be exemplary and illustrative, not limiting in scope.

In one aspect, a pharmaceutical composition suitable for intravenous administration is provided which comprises a stable emulsion comprising an oil phase, wherein the oil phase comprises a neurokinin 1 (NK-1) receptor antagonist, a surfactant and a co-surfactant; and an aqueous phase, wherein the aqueous phase comprises water, a tonicity agent, and a pH modifier.

In some embodiments, the NK-1 receptor antagonist is selected from the group consisting of aprepitant, rolapitant, netupitant, lanepitant, vestipitant, orvepitant maleate, casopitant, ezlopitant, serlopitant, befetupitant and maropitant, or a pharmaceutically acceptable salt thereof. In other embodiments, the NK-1 receptor antagonist is poorly soluble in water.

In some embodiments, the NK-1 receptor antagonist is selected from the group consisting of rolapitant, netupitant, casopitant, ezlopitant, vestipitant, serlopitant, maropitant, and orvepitant.

In some embodiments, the NK-1 receptor antagonist is not aprepitant.

In some embodiments, the composition is an oil-in-water emulsion comprising an oil wherein the oil is selected from the group consisting of coconut oil, olive oil, soybean oil, safflower oil, triglycerides, octyl and decyl glycerate, ethyl oleate, glyceryl linoleate, ethyl linoleate, glyceryl oleate, cholesteryl oleate/linoleate or a mixture thereof. In other embodiments, the oil is hydrolyzed. In still other embodiments, the oil is structurally modified.

In some embodiments, the emulsifier comprises a phospholipid. In another embodiment, the emulsifier is selected from the group consisting of egg phospholipids, soy phospholipids, phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In some embodiments, the co-surfactant comprises an alcohol. In other embodiments, the co-surfactant is ethanol.

In some embodiments, the pH modifier comprises an oleate or pharmaceutically acceptable salt thereof. In other embodiments, the oleate is sodium, potassium or ammonium oleate. In yet other embodiments, the pH modifier is sodium oleate or a pharmaceutically acceptable salt thereof.

In some embodiments, the pH modifier comprises a buffer. In other embodiments, the buffer is selected from the group consisting of phosphate buffer, citrate buffer, Tris buffer, carbonate buffer, succinate buffer, maleate buffer and borate buffer. In still other embodiments, the buffer is selected from the group, phosphate buffered saline (PBS), modified PBS (PBS-mod) and citrate buffer.

In some embodiments, the pH modifier comprises an oleate and a buffer. In other embodiments, the oleate is sodium oleate and the buffer is Tris buffer.

In some embodiments, the pH modifier is selected from the group consisting of sodium hydroxide, potassium hydroxide, magnesium hydroxide, sodium carbonate, Tris, sodium linoleate, sodium oleate, potassium oleate, ammonium oleate, potassium carbonate, potassium linoleate, and mixtures thereof.

In some embodiments, the composition comprises about 5 wt/wt % (weight/weight %) to 15 wt/wt %, 5 wt/wt % to 10 wt/wt %, 7 wt/wt % to 10 wt/wt %, 8 wt/wt % to 9 wt/wt %, or 9 wt/wt % to 10 wt/wt % oil. In another embodiment, the composition comprises about 8 wt/wt5, 8.5 wt/wt %, 9 wt/wt %, 9.5 wt/wt %, 10 wt/wt %, or 10.5 wt/wt % oil. In still other embodiments, the oil is soybean oil.

In some embodiments, the composition comprises about 10 wt/wt % to 20 wt/wt %, 12 wt/wt % to 17 wt/wt %, 13 wt/wt % to 16 wt/wt %, 13 wt/wt % to 15 wt/wt %, 14 wt/wt % to 15 wt/wt %, or 13 wt/wt % to 14 wt/wt % emulsifier. In other embodiments, the composition comprises about 13 wt/wt %, 13.5 wt/wt %, 14 wt/wt %, 14.5 wt/wt %, 15 wt/wt %, 16 wt/wt %, 17 wt/wt %, 18 wt/wt %, 19 wt/wt % or 20 wt/wt % emulsifier. In still other embodiments, the emulsifier is a lecithin. In other embodiments, the lecithin is an egg yolk lecithin.

In some embodiments, the composition comprises about 0.05 wt/wt % to 1.5 wt/wt %, 0.1 wt/wt % to 1.0 wt/wt %, 0.2 wt/wt % to 0.8 wt/wt %, 0.3 wt/wt % to 0.7 wt/wt %, 0.4 wt/wt % to 0.6 wt/wt %, 0.4 wt/wt % to 0.5 wt/wt % oleate or salt thereof. In other embodiments, the composition comprises about 0.05 wt/wt %, 0.1 wt/wt %, 0.2 wt/wt %, 0.3 wt/wt %, 0.4 wt/wt %, 0.45 wt/wt %, 0.5 wt/wt %, 0.6 wt/wt %, 0.7 wt/wt %, 0.8 wt/wt %, 0.9 wt/wt %, 1.0 wt/wt % or 1.5 wt/wt % oleate or salt thereof. In still other embodiments, the oleate is sodium oleate. In still another embodiment, the oleate or sodium oleate is the pH modifier.

In some embodiments, the composition comprises about 20 wt/wt % to 50 wt/wt %, 30 wt/wt % to 50 wt/wt %, 35 wt/wt % to 45 wt/wt %, 30 wt/wt % to 45 wt/wt %, 37 wt/wt % to 42 wt/wt %, 38 wt/wt % to 40 wt/wt %, 30 wt/wt %, 31 wt/wt %, 32 wt/wt %, 33 wt/wt %, 34 wt/wt %, 35 wt/wt %, 36 wt/wt %, 37 wt/wt %, 38 wt/wt %, 39 wt/wt %, 40 wt/wt %, 41 wt/wt %, 42 wt/wt %, 43 wt/wt %, 44 wt/wt %, 45 wt/wt %, 46 wt/wt %, 47 wt/wt %, 48 wt/wt %, 49 wt/wt %, 50 wt/wt % of oil expressed as a percentage of the weight of the oil per the sum of weight of oil, emulsifier and oleate in a unit of the composition. In other embodiments, the oil is soybean oil.

In some embodiments, the composition comprises about 20 wt/wt % to 50 wt/wt %, 30 wt/wt % to 50 wt/wt %, 35 wt/wt % to 45 wt/wt %, 30 wt/wt % to 45 wt/wt %, 37 wt/wt % to 42 wt/wt %, 38 wt/wt % to 40 wt/wt %, 30 wt/wt %, 31 wt/wt %, 32 wt/wt %, 33 wt/wt %, 34 wt/wt %, 35 wt/wt %, 36 wt/wt %, 37 wt/wt %, 38 wt/wt %, 39 wt/wt %, 40 wt/wt %, 41 wt/wt %, 42 wt/wt %, 43 wt/wt %, 44 wt/wt %, 45 wt/wt %, 46 wt/wt %, 47 wt/wt %, 48 wt/wt %, 49 wt/wt %, 50 wt/wt % of oil expressed as a percentage of the weight of the oil per the sum of weight of oil and emulsifier in a unit of the composition. In other embodiments, the oil is soybean oil.

In some embodiments, the composition comprises about 40 wt/wt % to 80 wt/wt %, 50 wt/wt % to 70 wt/wt %, 55 wt/wt % to 65 wt/wt %, 57 wt/wt % to 63 wt/wt %, 58 to 60 wt/wt %, 35 wt/wt % to 40 wt/wt %, 30 wt/wt % to 40 wt/wt %, 50 wt/wt %, 51 wt/wt %, 52 wt/wt %, 53 wt/wt %, 54 wt/wt %, 55 wt/wt %, 56 wt/wt %, 57 wt/wt %, 58 wt/wt %, 59 wt/wt %, 60 wt/wt %, 61 wt/wt %, 62 wt/wt %, 63 wt/wt %, 64 wt/wt %, 65 wt/wt %, 66 wt/wt %, 67 wt/wt %, 68 wt/wt %, 69 wt/wt %, 70 wt/wt % of emulsifier expressed as a percentage of the weight of emulsifier per the sum of weight of oil, emulsifier and oleate in a unit of the composition. In other embodiments, the emulsifier is a lecithin. In still other embodiments, the lecithin is an egg yolk lecithin.

In some embodiments, the composition comprises about 40 wt/wt % to 80 wt/wt %, 50 wt/wt % to 70 wt/wt %, 55 wt/wt % to 65 wt/wt %, 57 wt/wt % to 63 wt/wt %, 58 to 60 wt/wt %, 35 wt/wt % to 40 wt/wt %, 30 wt/wt % to 40 wt/wt %, 50 wt/wt %, 51 wt/wt %, 52 wt/wt %, 53 wt/wt %, 54 wt/wt %, 55 wt/wt %, 56 wt/wt %, 57 wt/wt %, 58 wt/wt %, 59 wt/wt %, 60 wt/wt %, 61 wt/wt %, 62 wt/wt %, 63 wt/wt %, 64 wt/wt %, 65 wt/wt %, 66 wt/wt %, 67 wt/wt %, 68 wt/wt %, 69 wt/wt %, 70 wt/wt % of emulsifier expressed as a percentage of the weight of emulsifier per the sum of weight of oil and emulsifier in a unit of the composition. In other embodiments, the emulsifier is a lecithin. In still other embodiments, the lecithin is an egg yolk lecithin.

In some embodiments, the ratio of oil to NK-1 receptor antagonist (wt %:wt %) in the composition ranges from about 5:1 to 20:1, 5:1 to 15:1, 5:1 to 10:1, 11:1 to 20:1, 11:1 to 15:1, 12:1 to 16:1, 12:1 to 14:1, 11:1 to 15:1, 12:1 to 14:1, 12.5:1 to 13.5:1, 13:1 to 14:1, or 12:1 to 15:1. In other embodiments, the ratio of oil to NK-1 receptor antagonist (wt %:wt %) in the composition is about 11:1 to 20:1, 11:1 to 15:1, 12:1 to 16:1, 12:1 to 14:1, 5:1, 6:1, 7:1, 8:1, 9:1, 10:1, 11:1, 11.5:1, 12:1, 12.5:1, 13:1, 13.5:1, 14:1, 14.5:1 or 15:1, 15.5:1, 16:1.

In some embodiments, the ratio of emulsifier to NK-1 receptor antagonist (wt %:wt %) in the composition ranges from about 10:1 to 30:1, 10:1 to 20:1, 15:1 to 30:1, 20:1 to 25:1, 18:1 to 22:1, 19:1 to 20:1, or 10:1 to 30:1. In other embodiments, the ratio of emulsifier:NK-1 receptor antagonist (wt %:wt %) in the composition is about 10:1, 11:1, 13:1, 14:1, 15:1, 18:1, 19:1, 20:1, 21:1, 22:1 23:1, 24:1, 25:1, or 30:1.

In some embodiments, the ratio of (emulsifier plus oil) to NK-1 receptor antagonist (wt %:wt %) in the composition ranges from about 20:1 to 40:1, 25:1 to 35:1, 30:1 to 35:1, or 32:1 to 34:1. In other embodiments, the ratio of (emulsifier plus oil) to NK-1 receptor antagonist is about 25:1, 26:1, 27:1, 28:1, 29:1 30:1, 31:1, 32:1, 33:1, 34:1, 35:1, 36:1, 37:1, 38:1 or 40:1.

In some embodiments, the ratio of emulsifier to oil (wt %:wt %) in the composition ranges from about 0.5:1, to 4:1, 1:1 to 2:1, 1.25:1 to 1.75:1, or 1.4:1 to 1.6:1. In other embodiments, the ratio of emulsifier to oil (wt %:wt %) in the composition is about 0.5:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 1.05:1, 1.15:1, 1.25:1, 1.35:1, 1.45:1, 1.55:1, 1.65:1, 1.75:1, 1.85:1, or 1.95:1.

In some embodiments, a therapeutic dose of the pharmaceutical composition comprises about 1 to 4 g, 1.5 to 3 g, 1.8 to 2.8 g, 2.3 to 2.8 g, 1.8 to 2.3 g, 1 g, 1.1 g, 1.2 g, 1.3 g, 1.4 g, 1.5 g, 1.6 g, 1.7 g, 1.8 g. 1.9 g, 2 g, 2.1 g, 2.2 g, 2.3 g, 2.4 g, 2.5 g, 2.6 g, 2.7 g, 2.8 g. 2.9 g, 3 g, 3.1 g, 3.2 g, 3.3 g, 3.4 g, 3.5 g, 3.6 g, 3.7 g, 3.8 g. 3.9 g, 4 g emulsifier. In other embodiments, the emulsifier is a lecithin. In still other embodiments, the emulsifier is egg yolk lecithin.

In some embodiments, a therapeutic dose of the pharmaceutical composition comprises about 0.5 to 3 g, 1 to 2.5 g, 1 to 2 g, 1 to 1.5 g, 1.5 g to 2 g, 0.5 g 0.6 g, 0.7 g, 0.8 g, 0.9 g, 1 g, 1.1 g, 1.2 g, 1.3 g, 1.4 g, 1.5 g, 1.6 g, 1.7 g, 1.8 g. 1.9 g, 2 g, 2.1 g, 2.2 g, 2.3 g, 2.4 g, 2.5 g oil. In other embodiments, the oil is soybean oil.

In some embodiments, a therapeutic dose of the pharmaceutical composition comprises about 50 to 600 mg, 100 to 600 mg, 100 to 500 mg, 100 to 400 mg, 100 to 300 mg, 100 to 200 mg, 200 to 400 mg, 50 to 250 mg, 75 to 200 mg, 100 to 150 mg, 100 mg, 110 mg, 120 mg, 130 mg, 140 mg, 150 mg, 160 mg, 170 mg, 180 mg, 190 mg, 200 mg, 250 mg, 300 mg, 350 mg, 400 mg, 450 mg, 500 mg, or 600 mg of the NK-1 receptor antagonist.

In some embodiments, the composition comprises about 0 wt/wt % to 10 wt/wt %, 1 wt/wt % to 9 wt/wt %, 2 wt/wt % to 6 wt/wt %, 2 wt/wt % to 4 wt/wt % or 2 wt/wt % to 3 wt/wt % co-surfactant. In other embodiments, the composition comprises less than 10 wt/wt %, less than 9 wt/wt %, less than 8 wt/wt %, less than 7, less than 6 wt/wt %, less than 5 wt/wt %, less than 4 wt/wt %, less than 3 wt/wt %, less than 2 wt/wt % or less than 1 wt/wt % co-surfactant.

In some embodiments, the composition comprises about 0 wt/wt % to 10 wt/wt %, 1 wt/wt % to 9 wt/wt %, or 2 wt/wt % to 6 wt/wt % ethanol. In other embodiments, the composition comprises less than 10 wt/wt %, less than 9 wt/wt %, less than 8 wt/wt %, less than 7, less than 6 wt/wt %, less than 5 wt/wt %, less than 4 wt/wt %, less than 3 wt/wt %, less than 2 wt/wt % or less than 1 wt/wt % ethanol.

In some embodiments, the aqueous phase of the emulsion comprises a tonicity agent, a pH modifier, and water.

In some embodiments, the aqueous phase of the emulsion comprises an osmotic agent, a pH modifier, and water.

In some embodiments, the aqueous phase of the emulsion comprises a tonicity agent, an osmotic agent, a pH modifier, and water.

In some embodiments, the aqueous phase further comprises a buffer.

In some embodiments, the aqueous phase comprises a buffer but does not comprise a pH modifier which is different from the buffer. In other embodiments, the buffer functions as both a pH modifier agent and a buffer.

In some embodiments, when the aqueous phase comprises a buffer, the composition contains no tonicity agent.

In some embodiments, the buffer is selected from the group consisting of phosphate buffer, citrate buffer, Tris buffer, carbonate buffer, succinate buffer, maleate buffer and borate buffer. In other embodiments, the buffer is selected from the group, phosphate buffered saline (PBS), modified PBS (PBS-mod) and citrate buffer.

In some embodiments, the aqueous phase comprises a buffer, that when mixed with the oil phase will provide a substantially isotonic oil in water emulsion.

In some embodiments, the osmotic agent is selected from the group consisting of glycerol, sorbitol, xylitol, mannitol, glucose, trehalose, maltose, sucrose, raffinose, lactose, dextran, polyethylene glycol, or propylene glycol. In other embodiments, the osmotic agent is an inorganic salt such as sodium chloride and mixtures thereof.

In some embodiments, the composition has a pH of about 6 to 9, 7 to 9, 7.5 to 9, 7.5 to 8.5, 8 to 9, 6 to 8, 7 to 8, or 6, 7, 8 or 9.

In some embodiments, the composition comprises about 0 wt/wt % to 25 wt/wt %, 2 wt/wt % to 20 wt/wt %, 3 wt/wt % to 15 wt/wt %, or 3 wt/wt % to 8 wt/wt % tonicity agent. In other embodiments, the composition comprises about 1 wt/wt %, 2 wt/wt %, 3 wt/wt %, 4 wt/wt %, 5 wt/wt %, 6 wt/wt %, 7 wt/wt %, 8 wt/wt %, 9 wt/wt %, or 10 wt/wt %, 11 wt/wt %, 12 wt/wt %, 13 wt/wt %, 14 wt/wt %, 15 wt/wt %, 16 wt/wt %, 17 wt/wt %, 18 wt/wt %, 19 wt/wt %, or 20 wt/wt %, 21 wt/wt %, 22 wt/wt %, 23 wt/wt %, 24 wt/wt %, 25 wt/wt % tonicity agent. In still other embodiments, the composition comprises no tonicity agent.

In some embodiments, the composition comprises about 0 wt/wt % to 25 wt/wt %, 2 wt/wt % to 20 wt/wt %, 3 wt/wt % to 15 wt/wt %, or 3 wt/wt % to 8 wt/wt % osmotic agent. In other embodiments, the composition comprises about 1 wt/wt %, 2 wt/wt %, 3 wt/wt %, 4 wt/wt %, 5 wt/wt %, 6 wt/wt %, 7 wt/wt %, 8 wt/wt %, 9 wt/wt %, or 10 wt/wt %, 11 wt/wt %, 12 wt/wt %, 13 wt/wt %, 14 wt/wt %, 15 wt/wt %, 16 wt/wt %, 17 wt/wt %, 18 wt/wt %, 19 wt/wt %, or 20 wt/wt %, 21 wt/wt %, 22 wt/wt %, 23 wt/wt %, 24 wt/wt %, 25 wt/wt % osmotic agent. In still other embodiments, the composition comprises no osmotic agent.

In some embodiments, the aqueous phase comprises a dose of dexamethasone sodium phosphate in a therapeutic dose of the pharmaceutical composition. In other embodiments, the dose of dexamethasone sodium phosphate ranges from about 0.5 mg to 30 mg, 0.5 mg to 25 mg, 1 mg to 20 mg, 10 mg to 20 mg, or 3 mg to 16 mg. In still other embodiments, the dose of dexamethasone sodium phosphate is about 9 mg or 16 mg in a therapeutic dose of the pharmaceutical composition. In these embodiments comprising a dose of dexamethasone, the therapeutic dose of the pharmaceutical composition comprises about 50 to 600 mg, 100 to 600 mg, 100 to 500 mg, 100 to 400 mg, 100 to 300 mg, 100 to 200 mg, 200 to 400 mg, 50 to 250 mg, 75 to 200 mg, 100 to 150 mg, 100 mg, 110 mg, 120 mg, 130 mg, 140 mg, 150 mg, 160 mg, 170 mg, 180 mg, 190 mg, 200 mg, 250 mg, 300 mg, 350 mg, 400 mg, 450 mg, 500 mg, or 600 mg of the NK-1 receptor antagonist.

In some embodiments, the oil phase comprises a dose of dexamethasone in a therapeutic dose of the pharmaceutical composition. In other embodiments, the dose of dexamethasone ranges from about 0.5 mg to 30 mg, 0.5 mg to 20 mg, 1 mg to 18 mg, 10 mg to 20 mg, or 3 mg to 16 mg. In other embodiments, the dose of dexamethasone is about 8 mg or 12 mg in a therapeutic dose of the pharmaceutical composition. In these embodiments comprising a dose of dexamethasone, the therapeutic dose of the pharmaceutical composition comprises about 50 to 600 mg, 100 to 600 mg, 100 to 500 mg, 100 to 400 mg, 100 to 300 mg, 100 to 200 mg, 200 to 400 mg, 50 to 250 mg, 75 to 200 mg, 100 to 150 mg, 100 mg, 110 mg, 120 mg, 130 mg, 140 mg, 150 mg, 160 mg, 170 mg, 180 mg, 190 mg, 200 mg, 250 mg, 300 mg, 350 mg, 400 mg, 450 mg, 500 mg, or 600 mg of the NK-1 receptor antagonist In some embodiments, the emulsion comprises about 0.002 wt/wt % to 0.2 wt/wt %, 0.003 wt/wt % to 0.16 wt/wt %, 0.02 wt/wt % to 0.1 wt/wt % dexamethasone sodium phosphate.

In some embodiments, the composition is a stable system maintaining an intensity-weighted mean particle size as determined by dynamic light scattering (DLS) of about 50 nm to 1000 nm, 50 to 500 nm, 50 nm to 400 nm, 50 nm to 300 nm, 50 nm to 200 nm or 50 nm to 100 nm. In another embodiment, the average droplet size is maintained below 500 nm for a period of at least 1 month, 3 months, 6 months, 9 months, 12 months, 2 years or 3 years at room temperature. In other embodiments, the average droplet size is maintained below 500 nm for a period of at least 1 month, 3 months, 6 months, 9 months, 12 months, 2 years or 3 years at 5° C.

In another aspect, a method for preparing an emulsion comprising an NK-1 receptor antagonist compound and suitable for parenteral administration is provided.

In some embodiments, the administration is intravenous administration.

In some embodiments, the method comprises: a) preparing an oil phase by dissolving the antagonist compound and an emulsifier in ethanol, then adding in oil to generate an oil-based mixture; b) preparing an aqueous phase by mixing water, optionally with a tonicity agent, optionally with an osmotic agent and optionally with a pH modifier and optionally with a buffer to generate an aqueous mixture; c) combining the oil-based mixture and the aqueous mixture and subjecting this to high speed homogenization to generate a crude emulsion; and d) subjecting the crude emulsion to high pressure homogenization to generate a fine emulsion.

In some embodiments, preparing the oil phase further comprises dissolving dexamethasone with the antagonist compound and the emulsifier in the ethanol.

In some embodiments, the method comprises: a) combining a NK-1 receptor antagonist, an emulsifier, and an alcohol with an oil to generate an oil phase; (b) combining water, a tonicity agent, a pH modifier, and optionally a buffer to generate an aqueous phase; (c) homogenizing the oil phase with the aqueous phase to generate the pharmaceutical emulsion; and (d) sterilizing the pharmaceutical emulsion. In other embodiments, the homogenizing comprises high speed homogenization.

In some embodiments, the method comprises: a) preparing an oil phase by dissolving the antagonist compound and an emulsifier in ethanol and oil to generate an oil-based mixture; b) preparing an aqueous phase by mixing water, optionally with a tonicity agent, optionally with an osmotic agent and optionally with a pH modifier and optionally with a buffer to generate an aqueous mixture; c) combining the oil-based mixture and the aqueous mixture and subjecting this to homogenization to generate a crude emulsion; and d) subjecting the crude emulsion to homogenization to generate a fine emulsion. In other embodiments, the subjecting the homogenization to generate a crude emulsion is high-speed homogenization. In still other embodiments, the homogenization to generate a fine emulsion is a high pressure homogenization.

In some embodiments, preparing the oil phase further comprises dissolving dexamethasone with the antagonist compound and the emulsifier in the ethanol and oil.

In some embodiments, preparing the aqueous phase further comprises mixing dexamethasone with the water, tonicity agent, pH modifier, and a buffer. In other embodiments, the dexamethasone is a salt of dexamethasone. In still other embodiments, the dexamethasone is dexamethasone sodium phosphate.

In some embodiments, the method further comprises sterilizing the fine emulsion to generate the final emulsion, wherein the final emulsion is suitable for injection into a subject.

In some embodiments, the dissolution in ethanol is performed at a temperature of about 25° C. to 80° C., 40° C. to 75° C., 60° C. to 70° C., or at about 25° C., 35° C., 45° C., 60° C., 65° C., 70° C. or 75° C.

In some embodiments, the high-speed homogenization is performed at a speed of about 2,000 rpm (revolutions per minute) to 25,000 rpm. In other embodiments, the high-speed homogenization is performed at a speed of about 20,000 rpm. In still other embodiments, the high-speed homogenization is performed at a speed of about 3600 rpm.

In some embodiments, the high-speed homogenization is performed for a time period of about 0.5 min to 1 hour, 1 min to 45 min, or 1 min to 30 min. In other embodiments, the high-speed homogenization is performed for a time period of about 20 to 40 min or for about 30 min.

In some embodiments, the high-speed homogenization is performed at about 10° C. to about 60° C., 20° C. to about 60° C., about 30° C. to about 50° C., or about 35° C. to about 45° C. In another embodiment, the high-speed homogenization is performed at about 25° C., 30° C., 35° C., 40° C., 45° C. or 50° C.

In some embodiments, the high-pressure homogenization is performed at a pressure of about 10,000 psi (pounds per square inch) to 30,000 psi. In other embodiments, the high-pressure homogenization is performed at a pressure of about 20,000 psi.

In some embodiments, the high-pressure homogenization is performed with cooling. In another embodiment, the high-pressure homogenization is performed with cooling which is sufficient to bring the temperature of the emulsion at the outlet of the process to about 0° C. to about 60° C., about 10° C. to about 40° C., about 20° C. to about 30° C., or to about 20° C., 25° C. or 30° C. within the time period.

In some embodiments, the sterilizing the fine emulsion comprises filtering the fine emulsion through a nylon filter. In other embodiments, the nylon filter is a Posidyne® filter. In yet another embodiment, the filter has a pore size of about 0.2 μm (micrometers).

In another aspect, the compositions described herein are for treatment of a subject, and the composition is administered via injection to a subject in need.

In some embodiments, the compositions are for use in a method for the treatment of emesis induced by a chemotherapeutic agent, by radiation-induced nausea and vomiting, and/or by post-operative induced nausea and vomiting in a subject. In other embodiments, the treatment comprises administering to the subject a composition comprising an NK-1 receptor antagonist as described herein. In still other embodiments, the compositions are for use in preventing or treating acute and delayed nausea and vomiting.

Additional embodiments of the present compositions and methods and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIG. 1A: Example 1, FIG. 1B: Example 2, FIG. 1C: Example 3, FIG. 1D: Example 6

DETAILED DESCRIPTION

Figure 1A:
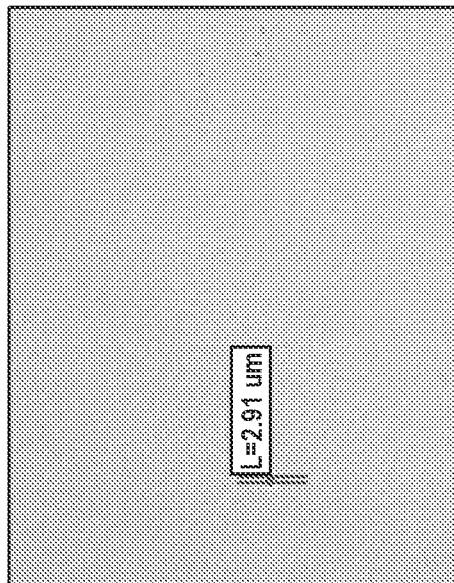
FIGS. 1A-1D provides microscope images of samples from Examples 1, 2, 3 and 6 after a freeze-thaw cycle.
Figure 1B:
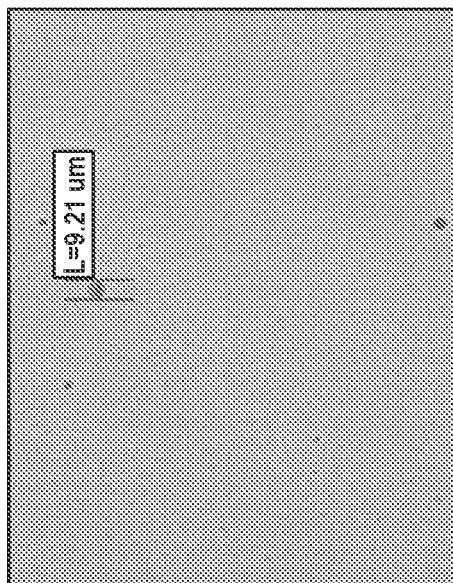

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm. As used herein, the term "about" means±5%, ±10%, or ±20% of the value being modified.

The term "emulsion" or "emulsion formulation" means a colloidal dispersion of two immiscible liquids in the form of droplets, whose diameter, in general, is between 10 nanometers and 100 microns. An emulsion is denoted by the symbol O/W (oil-in-water) if the continuous phase is an aqueous solution and by W/O (water-in-oil) if the continuous phase is an oil. Other examples of emulsions such as O/W/O (oil-in-water-oil) include oil droplets contained within aqueous droplets dispersed in a continuous oil phase.

"Physically stable" emulsions will meet the criteria under USP <729>, which defines universal limits for (1) mean droplet size not exceeding 500 nm or 0.5 μm and (2) the population of large-diameter fat globules, expressed as the volume-weighted percentage of fat greater than 5 μm (PFAT5) not exceeding 0.05%, at 5° C. or room temperature for a designated storage time period. In addition, physically stable emulsions will have no visible NK-1 receptor antagonist crystals upon storage at 5° C. or room temperature for a designated time period. Crystals are considered visible when viewed at magnification of 4× to 10×. An emulsion is physically stable if it meets the criteria under USP <729> and NK-1 receptor antagonist crystals are not visible upon storage at 5° C. or room temperature for a time period equal to or at least 1 week, 2 weeks, 4 weeks, 1 month, 2 months, 6 months, 1 year or 2 years.

"Chemically stable" emulsions of the disclosure are ones in which the concentration of the active component (i.e., the drug being delivered) does not change by more than about 20% under appropriate storage conditions for at least 1 month. In certain embodiments, the concentration the NK-1 receptor antagonist in an emulsion of the present disclosure does not change by more than about 5%, 10%, 15% or 20% under appropriate storage conditions for at least 1, 2, 3, 4, 5, 6, 9, 12, 15, 18, or 24 months.

In one example, the stable emulsion compositions of the disclosure are stable over a wide range of temperatures, e.g., −20° C. to 40° C. The compositions of the disclosure may be stored at about 5° C. to about 25° C.

"Oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase. The oil phase refers to the non-aqueous portion of a water-in-oil emulsion.

"Aqueous phase" or "water phase" in a water-in-oil emulsion refers to the water present and any components that are water soluble, i.e., have not exceeded their solubility limit in water. "Aqueous phase", as used herein, includes a water-containing liquid which can contain pharmaceutically acceptable additives such as acidifying, alkalizing, buffering, chelating, complexing and solubilizing agents, antioxidants and antimicrobial preservatives, humectants, suspending and/or viscosity modifying agents, tonicity and wetting or other biocompatible materials. The aqueous phase refers to the non-oil portion of a water-in-oil emulsion.

An "emulsifier" refers to a compound that deters the separation of the injectable emulsion into individual oil and aqueous phases. Emulsifiers useful in the present disclosure generally are (1) compatible with the other ingredients of the stable emulsions of the present disclosure, (2) do not interfere with the stability or efficacy of the drugs contained in the emulsions, (3) are stable and do not deteriorate in the preparation, and (4) are non-toxic.

Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids.

A "phospholipid" refers to a triester of glycerol in which the secondary alcohol and one of the primary alcohols has been esterified with fatty acids and the other primary alcohol has been esterified with a phosphate group. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipids can have any combination of fatty acid as its fatty acyl side chain, for example, the phospholipids can have a saturated fatty acid such as a decanoic acid, lauric acid, myristic acid, palmitic acid, stearic acid, icosanoic acid, (a C20 saturated fatty acid); sodium behenic acid, or an unsaturated fatty acid such as myristoleic acid, palmitoleic acid, oleic acid, sodium linoleic acid, alpha linolenic acid, sodium arachidonic acid, eicosapentanoic acid, and the like. The two fatty acyl residues on the phospholipids may be the same or they may be different fatty acids. The phospholipid component of the drug delivery composition can be either a single phospholipid or a mixture of several phospholipids. The phospholipids should be acceptable for the chosen route of administration.

In one aspect, the phospholipids used as emulsifiers in the present invention are naturally occurring phospholipids from a natural origin. For example, naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have been characterized in various compositions and are generally recognized to be safe, have combined emulsification and solubilization properties, and tend to be broken down into innocuous substances more rapidly than most synthetic surfactants.

The term "lecithin" includes a complex mixture of acetone-insoluble phosphatides, of which phosphatidylcholine is a significant component. The term lecithin is also used as a synonym for phosphatidylcholine. Useful lecithins include, but are not limited to, egg yolk-, egg-, soybean-, and corn-derived lecithin. In one embodiment, the emulsifier is lecithin, such as egg yolk-derived lecithin. The terms egg lecithin and egg yolk derived lecithin are used interchangeably throughout. The compositions described herein preferably comprise lecithin as an emulsifier.

The amount of phospholipids, by weight, in the emulsions of the present disclosure may be within a range of about 10 wt/wt % to about 20 wt/wt %, 11 wt/wt % to 19 wt/wt %, 11 wt/wt % to 15 wt/wt %, 12 wt/wt % to 13 wt/wt %, 13 wt/wt % to 14 wt/wt %, 13 wt/wt % to 20 wt/wt %, or 12 wt/wt % to 18 wt/wt %. In certain embodiments, the phospholipids in the emulsions are at a concentration, by weight, about 11 wt/wt %, 12 wt/wt %, 12.5 wt/wt %, 13 wt/wt %, 13.5 wt/wt %, 14 wt/wt %, 14.5 wt/wt %, or 15 wt/wt %.

"Oil" refers to an organic liquid of mineral, vegetable, animal, essential or synthetic origin, including, for example, aliphatic or wax-based hydrocarbons, aromatic hydrocarbons or mixed aliphatic and aromatic hydrocarbons.

The term "buffer" or "buffered" as used herein means a solution containing both a weak acid and its conjugate base, whose pH changes only slightly upon addition of acid or base. As used herein, the phrase "buffering agent" means a species whose inclusion in a solution provides a buffered solution. Buffers are well-known in the art and readily available. Buffers for use according to the methods and compositions described herein include but are not limited to phosphate, citrate, Tris, carbonate, succinate, maleate, borate, MES, Bis-Tris, ADA, aces, PIPES, MOPSO, Bis-Tri Propane, BES, MOPS, TES, HEPES, DIPSO, MOBS, TAPSO, Trizma, HEPPSO, POPSO, TEA, EPPS, Tricine, Gly-Gly, Bicine, GEPBS, TAPS, AMPD, TABS, AMPSO, CHES, CAPSO, AMP, CAPS, and CABS.

The term "therapeutic agent" describes any natural or synthetic compound which has a biological activity. A "therapeutically effective amount" means the amount that, when administered to an animal or subject for treating or preventing a disorder, condition, or disease, is sufficient to effect treatment for that disorder, condition, or disease.

As used herein, the term "emesis" includes nausea and vomiting.

The term "substantially" in reference to a certain feature or entity means to a significant degree or nearly completely (i.e. to a degree of 85% or greater) in reference to the feature or entity.

II. Nk-1 Reception Antagonist Emulsion and Methods of Making

The present disclosure is directed to stable pharmaceutical compositions including an NK-1 receptor antagonist, a surfactant or mixtures of surfactants, a co-surfactant, an oil, with an aqueous phase. The composition can be an injectable emulsion and is in the form of an oil-in-water emulsion which remains stable over an extended period of time and which is suitable for dilution and intravenous administration.

The NK-1 receptor antagonist compound is present in the oil phase with an emulsifier, a co-surfactant and an oil. The oil phase is then combined with an aqueous phase comprising water and a tonicity agent as described below to generate the stable emulsion. Prior to combining the oil phase with the aqueous phase, the oil phase will have an oil:antagonist compound ratio of about 11:1 to 30:1, 11:1 to 15:1, or about 13:11. For example, in formulating an oil phase comprising aprepitant, use of an oil:aprepitant ratio of about 13:1 was surprisingly found to produce, when mixed with the water phase, an emulsion which is more stable as compared to an emulsion in which the oil phase contains an oil:aprepitant ratio of less than about 12:1 or 11:1, and/or greater than about 15:1, 20:1, or 30:1. Accordingly, in some embodiments the stable emulsion comprising an NK-1 receptor antagonist and to be administered to the subject can have an oil:antagonist compound ratio of about 11:1 to 30, 11:1 to 15:1, or about 13:11. Also contemplated, however, are emulsions in which the oil:antagonist compound ratio is about 5:1 to 20:1, 5:1 to 15:1 or 5:1 to 10:1.

Moreover, the present compositions also possess favorable stability properties when the amount of emulsifier in the oil phase is greater than the amount of oil. For example, the oil phase contains an emulsifier:oil ratio of about 5:1 to 1:1, 3:1 to 1:1 or a ratio of about 1.5:1. Such ratios of emulsifier:oil have surprisingly been found to impart greater stability on a final emulsion which is suitable for injection into a patient. For example, an aprepitant emulsion having a phospholipid:oil ratio within the oil phase of about 1.5:1 was found to have greater stability than a similar aprepitant emulsion, wherein the oil phase comprises a phospholipid:oil ratio of about 0.01:1, 0.1:1, 0.5:1 or 0.9:1.

Suitable NK-1 receptor antagonists for use in the presently described pharmaceutical emulsions include RP 67580 ((3aR,7aR)-Octahydro-2-[1-imino-2-(2-methoxyphenyl) ethyl]-7,7-diphenyl-4H-isoindol)), WIN 51078 (17-β-Hydroxy-17-α-ethynyl-5-α-androstano[3,2-b]pyrimido[1,2-a] benzimidazole), 1-733,060, (((2S,3S)-3-[[3,5-bis (Trifluoromethyl)phenyl]methoxy]-2-phenylpiperidine hydrochloride), 1-703,606 (cis-2-(Diphenylmethel)-N-([2-iodophenyl]methyl)-1-azabicyclo(2.2.2)octan-3-amine)

MDL 105,212 (R)-1-[2-[3-(3,4-dichlorophenyl)-1-(3,4,5-trimethoxybenzoyl)-pyrrolidin-3-yl]-ethyl]-4-phenylpiperidine-4-carboxamide hydrochloride), serlopitant, maropitant, Antagonist D, aprepitant, fosaprepitant, R116301, CGP49823, CP-96345, CP-99994, GR-203040, MDL-103392, 1-760735, SDZ-NKT-343, nolpitanitium (SR-140333), AV608, rolapitant, SCH 900978, AV608, GSK424887 (GlaxoSmithKline), GSK206136 (GlaxoSmithKline), GR-205171, CP-99994, TAK 637 ((S)-7-(3,5-Bis-trifluoromethyl-benzyl)-9-methyl-5-p-tolyl-8,9,10,11-tetrahydro-7H-1,7,11a-triaza-cycloocta[b]naphthalene-6,12-dione), LY303870 ([(R)-1-[N-(2-methoxybenzyl)acetylamino]-3-(1H-indol-3-yl)-2-[N-(2-(4-(piperidin-1-yl)piperidin-1-yl)acetyl)amino]propane]), LY686017 ((2-chloro-phenyl)-{2-[5-pyridin-4-yl-1-(3,5-bistrifluoromethyl-benzyl)-1H-[1,2,3]triazol-4-yl]-pyridin-3-yl}-methanone), E-6006, casopitant/GW679769 ((2R,4S)-4-(4-acetylpiperazin-1-yl)-N-[(1R)-1-[3,5-bis(trifluoromethyl)phenyl)ethyl]-2-(4-fluoro-2-methylphenyl)-N-methylpiperidine-1-carboxamide), vestipitant, orvepitant and orvepitant maleate, befetupitant, netupitant, ezlopitant, CP-122721, MPC-4505 (Myriad Genetics, Inc.), CP-122721 (Pfizer, Inc.), CJ-1 2,255 (Pfizer, Inc.), SRR 240600 (Sanofi-Aventis), or TA-5538 (Tanabe Seiyaku Co.) including all pharmaceutically acceptable salts thereof.

1. Oil Phase

The oil (hydrophobic) phase comprises an oil. Triglycerides are exemplary oils for use in the compositions described herein. In certain embodiments the oil is or comprises a vegetable oil. "Vegetable oil" refers to oil derived from plant seeds or nuts. Vegetable oils are typically "long-chain triglycerides" (LCTs), formed when three fatty acids (usually 14 to 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are used to ensure safety and stability of the oil-in-water emulsions. In certain embodiments hydrogenated vegetable oils, which are produced by controlled hydrogenation of the vegetable oil, may be used. Exemplary vegetable oils include but are not limited to almond oil, babassu oil, black currant seed oil, borage oil, canola oil, castor oil, coconut oil, corn oil, cottonseed oil, olive oil, peanut oil, palm oil, palm kernel oil, rapeseed oil, safflower oil, soybean oil, sunflower oil and sesame oil. Hydrogenated and/or or partially hydrogenated forms of these oils may also be used. In specific embodiments, the oil is or comprises safflower oil, sesame oil, corn oil, olive oil and/or soybean oil. In more specific embodiments, the oil is or comprises safflower oil, and/or soybean oil. The oil is present in the emulsion at about 9 wt/wt %, though this may vary between about 5 wt/wt % to 12 wt/wt % or 9 wt/wt % to 10 wt/wt %.

To generate the oil phase, the NK-1 receptor antagonist is first mixed with an emulsifier such as a phospholipid emulsifier. Examples 1-6 and 11-19 are examples in which NK-1 receptor antagonist emulsions made using an egg lecithin. A phospholipid emulsifier is added to a concentration of greater than 10 wt/wt %, 11 wt/wt %, 12 wt/wt % or 13 wt/wt % of the emulsion but less than 15 wt/wt %, 17 wt/wt % or 20 wt/wt % of the emulsion.

The mixture of antagonist and emulsifier is dissolved in a co-surfactant such as a short chain alcohol (1 to 6 carbons). Examples 1-6 and 11-19 below are some examples in which the co-surfactant is ethanol. The mixture is mixed at an elevated temperature, such as at about 60° C. or 70° C. or at an elevated temperature within the range of about 50° C. or 70° C., until the NK-1 receptor antagonist and emulsifier are dissolved. This mixture is then combined with the oil, such as soybean oil, by mixing again at an elevated temperature such as at about 60° C. to produce the oil phase containing the NK-1 receptor antagonist. Excess co-surfactant can be removed by standard evaporation methods including heating, or pressure reduction, or a combination thereof such employed in a rotary evaporator. In this process, about 10% to 100%, 20% to 95%, 80% to 100%, 90% to 100%, or 95% to 100% of the ethanol evaporates depending on preparation scale, any pressure reduction, and heating time.

In one embodiment, the NK-1 receptor antagonist and the emulsifier are dissolved in a co-surfactant and an oil. Examples 1-6 and 11-19 below are some examples in which the co-surfactant is ethanol and the oil is soybean oil, however, the methods can be used with any one or more of the co-surfactants and oils described herein. The mixture is mixed at an elevated temperature, such as at about 60° C. or 70° C. or at an elevated temperature within the range of about 50° C. or 70° C., at least until the NK-1 receptor antagonist and emulsifier are dissolved to produce the oil phase containing the NK-1 receptor antagonist. The mixture of NK-1 receptor antagonist, emulsifier, co-surfactant and oil are mixed at the elevated temperature for about 15 min to 120 min, about 15 min to 45 min, about 30 min to 90 min, or for about 15 min, 30 min or 50 min.

Excess co-surfactant can be removed by standard evaporation methods including heating, or pressure reduction, or a combination thereof in a rotary evaporator. During this process, about 10% to 100%, 20% to 95%, 80% to 100%, 90% to 100%, or 95% to 100% of the ethanol evaporates depending on preparation scale, any pressure reduction, and heating time.

In one embodiment, dexamethasone is added to the oil phase comprising the NK-1 receptor antagonist, emulsifier and oil to generate an oil phase comprising both the NK-1 receptor antagonist and dexamethasone prior to mixing with the aqueous phase to generate the pharmaceutical emulsion for injection. Dexamethasone is added to the oil phase to provide a dose of about 12 mg dexamethasone.

2. Aqueous Phase

The aqueous phase of the NK-1 receptor antagonist emulsion can be a mixture of water and a tonicity agent, including those such as but not limited to sucrose, mannitol, glycerin or dextrose or a mixture thereof. Also included in the aqueous phase is a pH-modifying agent (pH modifier). Sodium oleate is used in Examples 1-3, 5, 6, and 11-15, and 17-19 below to adjust the pH of the emulsion to about 6 to 9, depending on the desired emulsion formulation. However, it is understood that the pH modifier can be other oleic acids or salts thereof including but not limited to sodium oleate, potassium oleate and ammonium oleate. The oleic acid can comprise about 0.1 wt/wt % to 1.0 wt/wt % or about 0.4 wt/wt % or 0.5 wt/wt % of the stable injectable emulsions as provided herein. The aqueous phase is produced by mixing water with the tonicity agent and pH modifier (e.g., sodium oleate). Additional pH modifiers that may be used include but are not limited to sodium hydroxide, potassium hydroxide, magnesium hydroxide, Tris, sodium carbonate and sodium linoleate. In some embodiments, the pH modifier comprises more than one pH modifier. For example, the aqueous phase may comprise both an oleate and a buffer such as a Tris buffer. The pH modifier used is effective for adjusting the pH of the emulsion to a preferred pH of about 6 to 9, 7 to 8, or about 6, 7, 8 or 9. The aqueous phase can readily form by mixing at room temperature.

The aqueous phase of the emulsion may further contain a buffering agent to promote stability of the emulsion formulation. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation. Thus, pH should be controlled during manufacture and emulsion formulations may include a buffering agent to provide additional control. Any decrease in pH over the assigned shelf-life may be indicative of chemical degradation. Suitable buffers are well known to the person skilled in the art and include but are not limited to a phosphate buffer, citrate buffer, Tris buffer, carbonate buffer, succinate buffer, maleate buffer or borate buffer. Tris buffer is used in Examples 11 and 19 below to adjust the pH of the emulsion to about 8 to 9. As shown in Examples 11 and 19, in some embodiments a buffer such as Tris buffer can be used in addition to another pH modifier (e.g., oleate or sodium oleate) to adjust or modify the pH of the emulsion. In some embodiments, the buffer is selected from the group, phosphate buffered saline (PBS), modified PBS (PBS-mod) and citrate buffer. In a particular embodiment, the aqueous phase comprises a buffer, that when mixed with the oil phase will provide a substantially isotonic oil in water emulsion.

Buffering agents useful for the presently described compositions include, but are not limited to, a phosphate buffer, citrate buffer, Tris buffer, carbonate buffer, succinate buffer, maleate buffer or borate buffer. In a particular embodiment, the buffer is selected from the group, phosphate buffered saline (PBS), modified PBS (PBS-mod) and citrate buffer. In a particular embodiment, the aqueous phase comprises a buffer, that when mixed with the oil phase will provide a substantially isotonic oil in water emulsion. In some embodiments, when the aqueous phase contains a buffering agent, the aqueous phase does not include a tonicity agent. Also, when a buffer is added to the aqueous phase, a pH-adjusting agent may not be added to the aqueous phase. It is understood that a buffer can be added to the aqueous phase or the buffer can be added to the emulsion.

In some embodiments, the aqueous phase of the emulsion contains a tonicity agent such as sucrose. The tonicity agent is added to an aqueous phase having about 0% to 30%, 0% to 25% or about 20% of the tonicity agent (wt/wt). It was surprisingly found that a composition containing about 20% sucrose wt/wt in the aqueous phase produced an emulsion that was particularly stable as determined by freeze-thaw testing. Accordingly, preferred embodiments include an emulsion in which the aqueous phase comprises a tonicity agent which imparts greater chemical and/or physical stability as compared to an emulsion wherein the aqueous phase contains less than about 10%, 15% or 20% wt/wt tonicity agent or more than about 30%, 40% or 50% wt/wt tonicity agent.

In one embodiment, the aqueous phase further comprises dexamethasone sodium phosphate (also referred to as "dexamethasone phosphate"). Dexamethasone sodium phosphate is a corticosteroid which is freely soluble in water. Daily dosages for dexamethasone sodium phosphate range from about 0.5 mg to 20 mg, more preferably from about 14 mg to 18 mg or 16 mg, depending on the severity of the disease or disorder. Accordingly, an NK-1 receptor antagonist emulsion further comprising dexamethasone may contain dexamethasone sodium phosphate in the aqueous phase. Accordingly, the aqueous phase of an emulsion suitable for intravenous administration may contain about 0.5 mg to 20 mg, 14 mg to 18 mg or about 16 mg dexamethasone sodium phosphate.

In another embodiment, a solution of dexamethasone sodium phosphate can be mixed into the fine emulsion prior to sterile filtration to prepare an emulsion containing dexamethasone sodium phosphate in the aqueous phase, 3. Pharmaceutical Emulsion Formulations The pharmaceutical compositions comprising NK-1 receptor antagonists as disclosed herein are sterile oil-in-water emulsions comprising the aqueous and oil phases described above. Also encompassed by the disclosure are methods for preparing stable emulsions comprising the receptor antagonist which are suitable for intravenous administration and which can be prepared according to the conventional manufacturing procedures using aseptic techniques.

The aqueous phase is combined with the oil phase, under high-speed homogenization to produce a coarse emulsion. Examples 1-6 and 12-19 provide examples of NK-1 receptor antagonist emulsions which are produced using compositions and methods disclosed herein. As described in these examples, the combined aqueous and oil phases is homogenized using an IKA Ultra-Turrax T25 dispersing instrument at a speed of 20,000 rpm for 1 min. The speed used in this first homogenization step may vary, for example, from 2000 rpm to 25,000 rpm, or from 15,000 rpm to 22,000 rpm. The time of the homogenization step can also vary, for example, from 0.5 min to 1 hour, or from 1 min to 45 min. This crude emulsion is then homogenized into a fine emulsion by a high-pressure homogenizer, which may be a microfluidizer. The interaction chamber and the cooling coil portions of the microfluidizer are cooled by water, such as by an ice bath. The temperature of the ice bath may be between 0 to 10° C., or 2 to 6° C. The temperature of the emulsion coming out of the high-pressure homogenization may be between 0 to 60° C., 15° C., to 60° C., 20° C. to 40° C., or at about 25° C. The microfluidizer is first primed with water and then the crude emulsion is introduced. The output from the homogenizer is initially run to waste to remove priming water, and priming water and emulsion mixtures, and then collected in a clean vessel when the stream becomes consistent in appearance. The high-pressure homogenizer cycle may be repeated to sufficiently reduce oil droplet size. The pressure used for the homogenization may vary. The pressures may be between 5000 and 30,000 psi. The number of passes through the microfluidizer may vary in order to achieve the desired droplet size. The number of passes may be from about 2 to 20, 2 to 15, 4 to 15, 4 to 12 or 7 to 8.

The pharmaceutical formulation may then be passed through a filter system at room temperature, and/or autoclaved, to achieve sterilization. The filters used to achieve sterilization may be chosen by the skilled artisan and may have a nominal pore size of 0.2 μm. The filter material used may vary. In one embodiment, the filter is nylon. In another embodiment, the filter is a Posidyne® filter (covalent charge-modified Nylon 6,6 membrane which exhibits a net positively-charged zeta potential in aqueous solutions). For large scale production the method above may need to be modified. A skilled practitioner could combine these materials in a different order and using different processing equipment to achieve the desired end result.

In one embodiment of the disclosure, the homogenization can be done in repeated cycles to achieve an emulsion in which the oil particle/globule size is less than 2 microns (μm) with intermediate cooling of the homogenized product to a temperature less than about 25° C.

The final emulsion comprises an oil portion (oil phase) dispersed in an aqueous portion (aqueous phase). The ratio of components to the NK-1 receptor antagonist within the oil phase is an important characteristic of the emulsion which may affect stability of the formulation prepared for injection and each of these ratios within the final pharmaceutical emulsion are presented in more detail below. As described above, the oil phase comprises the NK-1 receptor antagonist, an oil and an emulsifier, examples of which are provided herein.

The final emulsion contains about 0.7 wt/wt % of the NK-1 receptor antagonist, but may range from about 0.2 wt/wt % to 1.5 wt/wt %, 0.4 wt/wt % to 1.0 wt/wt %, 0.6 wt/wt % to 0.7 wt/wt %, or 0.7 wt/wt % to 0.8 wt/wt %. The emulsion is prepared which can contain about 130 mg of the NK-1 receptor antagonist, however, preparations may also be prepared according to the present disclosure which contain about 100 mg to 1000 mg, 100 mg to 500 mg, 250 mg to 750 mg or 100 mg to 200 mg NK-1 receptor antagonist.

In one embodiment, the ratio of oil:NK-1 receptor antagonist (wt %:wt %) within the oil phase of the final emulsion is about 13:1 to 14:1, but can range from about 11:1 to 15:1, 12:1 to 14:1, 13:1 to 13.5:1, or 12:1 to 15:1. In another embodiment, the ratio of oil:NK-1 receptor antagonist is about 11:1, 11.5:1, 12:1, 12.5:1, 13:1, 13.5:1, 14:1, 14.5:1 or 15:1.

The ratio of emulsifier to NK-1 receptor antagonist in the final emulsion can be about 20:1 but may also vary. For example, the ratio of emulsifier:NK-1 receptor antagonist (wt %:wt %) within the oil portion ranges from about 15:1 to 30:1, 20:1 to 25:1, 18:1 to 22:1, 19:1 to 20:1, or 10:1 to 30:1. In one embodiment, the emulsifier:NK-1 receptor antagonist (wt %:wt %) is about 15:1, 18:1, 19:1, 20:1, 21:1, 22:1 or 23:1.

The ratio of components within the oil phase of the final emulsion may alternatively be expressed in the ratio of (emulsifier plus oil):NK-1 receptor antagonist (wt %:wt %). The ratio of (emulsifier plus oil):NK-1 receptor antagonist can be about 33:1, but the ratios for the present emulsion can range from about 20:1 to 40:1, 25:1 to 35:1, 30:1 to 35:1 or 33:1 to 37:1, or may be, for example, about 30:1, 32:1, 33:1, 34:1, 35:1, 36:1, 37:1, 38:1 or 40:1.

The composition of the present disclosure has a significant advantage in terms of reduced toxicity as compared to injectable formulations which may contain less desirable excipients such as detergents, e.g., Tween-20 or Tween-80. The present formulations take advantage of the ability to solubilize therapeutically effective amounts of a NK-1 receptor antagonist in an oil phase which can then be used to generate an emulsion suitable for injection. Accordingly, described herein are pharmaceutical emulsion compositions containing a NK-1 receptor antagonist and optionally dexamethasone or dexamethasone sodium phosphate, wherein the emulsion does not comprise a detergent.

The composition of the present disclosure gives a product suitable for parenteral use because of low particle size. The composition of the present disclosure is easy to use as the product can be diluted with an agent such as an aqueous solution of sucrose, an aqueous solution of maltose or dextrose 5% injection or normal saline to achieve the required concentration for parenteral administration. The composition of the present disclosure also has a prolonged shelf life and hence is suitable for a readily marketable product.

The compositions of the disclosure are both chemically and physically stable. A physically stable emulsion of the invention is one which can be stored under appropriate conditions for at least 1, 2, 3, 4, 5, 6, 9, 12, 15, 18, 24 or 36 months, without an increase in average droplet size above that allowed as stated in USP <729>. As well, the population of large-diameter fat globules should be within the limits stated in USP <729>.

Droplet size limits defined in USP <729> apply throughout the assigned shelf life, which for a commercial pharmaceutical formulation may extend to 2-3 years or longer. All true emulsions are thermodynamically unstable and may over time undergo a range of processes which tend to increase the droplet size. These include direct droplet coalescence, when two droplets collide and form a single new droplet, and aggregation, in which droplets adhere together to form larger masses. Aggregation may in some cases be a precursor of further coalescence into larger droplets. These processes may result in large aggregates rising to the surface of the container, a phenomenon known as 'creaming', and ultimately to free oil being visible on the emulsion surface, known as 'cracking'.

Droplet size limits are typified by USP33-NF28 General Chapter <729> for Globule Size Distribution in Lipid Injectable Emulsions, hereinafter referred to as USP <729>, which defines universal limits for (1) mean droplet size not exceeding 500 nm or 0.5 μm and (2) the population of large-diameter fat globules, expressed as the volume-weighted percentage of fat greater than 5 μm (PFAT5) not exceeding 0.05%, irrespective of the final lipid concentration.

Droplet size measurements such as those defined in USP<729> can measure the initial increases in size, and hence are predictive of emulsion physical stability, at early times, long before the formulation shows macroscopic visible changes. Accordingly, the emulsions as described herein are stable compositions having an intensity-weighted mean droplet diameter less than about 500 nm, 400 nm, 300 nm, 200 nm or 100 nm.

The oil or particle droplet size, i.e. diameter, according to the present disclosure is measured using a dynamic light scattering (DLS) instrument, such as the Malvern Zetasizer 4000, Malvern Zetasize Nano S90 or preferably the Malvern Zetasizer Nano ZS. Intensity-weighted particles sizes were recorded, since they do not require the knowledge of the refractive index of the particle. In Malvern Zetasizer instruments, there are two fits for determining the intensity-weighted diameter of the oil droplet size. The first is a cumulant fit that is used to determine the Z-average diameter; this fit can additionally give the polydispersity index (PDI). This cumulant fit is recommended for monodisperse samples possessing a PDI of lower than 0.2. The second is a non-negative least squares (NNLS) fit. This gives the Peak 1 diameter, Peak 2 diameter and Peak 3 diameter. This is more suitable for polydisperse samples having a PDI of greater than 0.2.

The emulsion preparations as described herein may further comprise a preservative in quantities that preserve the composition. Suitable preservatives used in some of the embodiments of present disclosure include, but are not limited to, disodium edetate, tocopherol, benzalkonium chloride, methyl, ethyl, propyl or butylparaben, benzyl alcohol, phenylethyl alcohol, benzethonium, chlorobutanol, potassium sorbate or combination thereof.

III. MEDICAL USE

The pharmaceutical compositions of the present disclosure can be used for the prevention or treatment of emesis and provide a non-oral option for patients undergoing highly or moderately emetogenic chemotherapy such as chemotherapy used in cancer patients. The disclosure thus encompasses a method of treatment comprising intravenously administering an emulsion comprising a NK-1 receptor antagonist as described herein to a subject undergoing highly or moderately emetogenic chemotherapy whether the chemotherapy is an initial treatment or repeat courses of the chemotherapy. The pharmaceutical emulsions described herein can be used, for example, in preventing or treating acute and delayed nausea and vomiting associated with the chemotherapy or radiotherapy.

Another embodiment relates to the use of the pharmaceutical formulations of the disclosure in the manufacture of a medicament for use preventing or treating emesis in a subject in need thereof.

The amount of the NK-1 receptor antagonist and optionally dexamethasone required for use in the methods of the disclosure may vary with the method of administration and condition of the patient, and the degree of therapy required, and will be ultimately at the discretion of the attendant physician or clinician.

IV. EXAMPLES

The following examples are illustrative in nature and are in no way intended to be limiting.

Example 1: Preparing Aprepitant Emulsions for Intravenous Injection

To prepare the aprepitant emulsion, an oil phase was first prepared by combining 750 mg of aprepitant and 15.0 g of egg lecithin (LIPOID E 80) with 12.0 ml of ethanol. This mixture was dissolved by heating and stirring at 60° C. and 200 rpm for 15 min. To the resultant solution was added in 10.0 g of soybean oil. Heating at 60° C. and stirring at 200 rpm was continued for another 15 min. The aqueous phase was prepared by dissolving 5.60 g of sucrose and 0.500 g of sodium oleate in 70.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 1 below. By dynamic light scattering (Malvern® Zetasizer Nano ZS), the intensity-weighted particle size analyzed using non-negative least squares (NNLS) fit gave a Peak 1 diameter of 99 nm. The intensity-weighted mean particle size determined using cumulant fit provided a Z-average diameter of 87 nm. The zeta potential was measured to be −43 mV by laser Doppler micro-electrophoresis (Malvern® Zetasizer Nano ZS). The pH of the injectable emulsion was 8.74. This aprepitant-containing emulsion can be injected as is, or diluted for infusion with 5% dextrose or 0.9% saline.

TABLE 1

| Component | Amount (g) | Concentration (w/w %) | Ratio to Aprepitant |
| --- | --- | --- | --- |
| Aprepitant | 0.750 | 0.679 | 1 |
| Lipoid E 80 | 15.0 | 13.6 | 20 |
| Soybean Oil | 10.0 | 9.05 | 13.3 |
| Ethanol[1] | 8.59 | 7.78 | 11.5 |

TABLE 1-continued

| Component | Amount (g) | Concentration (w/w %) | Ratio to Aprepitant |
| --- | --- | --- | --- |
| Sucrose | 5.60 | 5.07 | 7.5 |
| Sodium Oleate | 0.500 | 0.453 | 0.667 |
| Water for Injection | 70.0 | 63.4 | 93.3 |
| Total | 110 | 100 | — |

[1]Final amount after taking into account the ethanol that was evaporated during processing.

Example 2: Preparing Aprepitant Emulsions for Intravenous Injection

To prepare the aprepitant emulsion, an oil phase was first prepared by combining 450 mg of aprepitant and 9.00 g of egg lecithin (LIPOID E 80) with 4.0 ml of ethanol. This mixture was dissolved by heating and stirring at 60° C. and 200 rpm for 15 min. To the resultant solution was added 6.00 g of soybean oil. Heating at 60° C. and stirring at 200 rpm was continued for another 15 min. The aqueous phase was prepared by dissolving 3.36 g of sucrose and 0.300 g of sodium oleate in 42.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 2 below. By dynamic light scattering (Malvern® Zetasizer Nano ZS), the intensity-weighted particle size analyzed using NNLS fit gave a Peak 1 diameter of 127 nm. The intensity-weighted mean particle sized determined using cumulant fit provided a Z-average diameter of 101 nm. The zeta potential was measured to be −47 mV by laser Doppler micro-electrophoresis (Malvern® Zetasizer Nano ZS). The pH of the injectable emulsion was 8.77. This aprepitant-containing emulsion can be injected as is, or diluted for infusion with 5% dextrose or 0.9% saline.

TABLE 2

| Component | Amount (g) | Concentration (w/w %) | Ratio to Aprepitant |
| --- | --- | --- | --- |
| Aprepitant | 0.450 | 0.714 | 1 |
| Lipoid E 80 | 9.00 | 14.3 | 20 |
| Soybean Oil | 6.00 | 9.52 | 13.3 |
| Ethanol[1] | 1.89 | 3.00 | 4.20 |
| Sucrose | 3.36 | 5.33 | 7.47 |
| Sodium Oleate | 0.300 | 0.476 | 0.667 |
| Water for Injection | 42.0 | 66.7 | 93.3 |
| Total | 63.0 | 100 | — |

[1]Final amount after taking into account the ethanol that was evaporated during processing.

Example 3: Preparing Aprepitant Emulsions for Intravenous Injection

To prepare the aprepitant emulsion, an oil phase was first prepared by combining 450 mg of aprepitant and 9.00 g of egg lecithin (LIPOID E 80) with 6.0 ml of ethanol. This mixture was dissolved by heating and stirring at 60° C. and 200 rpm for 15 min. To the resultant solution was added in 6.00 g of soybean oil. Heating at 60° C. and stirring at 200 rpm was continued for another 15 min. The aqueous phase was prepared by dissolving 15.62 g of sucrose and 0.300 g of sodium oleate in 42.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 3 below. By dynamic light scattering (Malvern® Zetasizer Nano ZS), the intensity-weighted particle size analyzed using NNLS fit gave a Peak 1 diameter of 88 nm. The intensity-weighted mean particle sized determined using cumulant fit provided a Z-average diameter of 68 nm. The zeta potential was measured to be −42 mV by laser Doppler micro-electrophoresis (Malvern® Zetasizer Nano ZS). The pH of the injectable emulsion was 8.80. This aprepitant-containing emulsion is to be diluted with water for injection by 4-fold prior to injection.

TABLE 3

| Component | Amount (g) | Concentration (w/w %) | Ratio to Aprepitant |
|---|---|---|---|
| Aprepitant | 0.450 | 0.587 | 1 |
| Lipoid E 80 | 9.00 | 11.7 | 20 |
| Soybean Oil | 6.00 | 7.83 | 13.3 |
| Ethanol[1] | 3.27 | 4.26 | 7.26 |
| Sucrose | 15.6 | 20.4 | 34.7 |
| Sodium Oleate | 0.300 | 0.391 | 0.667 |
| Water for Injection | 42.0 | 54.8 | 93.3 |
| Total | 76.6 | 100 | — |

[1]Final amount after taking into account the ethanol that was evaporated during processing.

Example 4: Preparing an Alternate Aprepitant Emulsion Formulation for Intravenous Injection An aprepitant emulsion was prepared which has less than 10% wt/wt of the phospholipid emulsifier and which was adjusted to a pH of less than 8.0. To prepare the aprepitant emulsion, an oil phase was first prepared by combining 450 mg of aprepitant and 6.67 g of egg lecithin (LIPOID E 80) with 7.2 ml of ethanol. This mixture was dissolved by heating and stirring at 60° C. and 200 rpm. Heating and stirring was carried out until the ethanol was evaporated and a thick residue was observed. To the resultant solution was added in 6.00 g of soybean oil and an appropriate amount of ethanol to obtain a clear oil phase upon heating at 60° C. The aqueous phase was prepared by dissolving 3.36 g of sucrose in 50.5 ml of water for injection at 60° C. The aqueous phase was then added to the oil phase and subsequently subjected to high-speed homogenization (Ultra-Turrax® IKA T25) at a speed of 20,000 rpm for 1 min to produce the crude emulsion. The pH of this crude emulsion was adjusted to 7.0 and then passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 4 below. Within 4 days post preparation at room temperature, crystals were observed in the product by microscopy.

TABLE 4

| Component | Amount (g) | Concentration (w/w %) | Ratio to Aprepitant |
|---|---|---|---|
| Aprepitant | 0.450 | 0.672 | 1 |
| Lipoid E 80 | 6.67 | 9.95 | 14.8 |
| Soybean Oil | 6.00 | 8.96 | 13.3 |
| Sucrose | 3.36 | 5.02 | 7.47 |
| Water for Injection | 50.5 | 75.4 | 112 |
| Total | 67.0 | 100 | — |

Example 5: Preparing Aprepitant Emulsions for Intravenous Injection

An aprepitant emulsion was prepared which contains oleic acid. To prepare the aprepitant emulsion, an oil phase was first prepared by combining 250 mg of aprepitant, 2.50 g of egg lecithin (LIPOID E 80), 15.0 g of soybean oil and 125 mg of oleic acid. Ten ml of ethanol was added to dissolve the mixture at 70° C. The ethanol was removed by pressure reduction in a 70° C. water bath to yield a clear oil phase. A preheated aqueous phase containing 82.1 ml of water for injection at 70° C. was added to the oil phase and subsequently subjected to high-speed homogenization (Ultra-Turrax® IKA T25) at a speed of 20,000 rpm for 1 min to produce the crude emulsion. This crude emulsion was passed 8 times through an ice-cooled high-pressure microfluidizer (Microfluidizer® M-110L, F12Y interaction chamber) at a pressure of 18,000 psi. The resultant fine emulsion was sterilized by passing it through a 0.2 μm nylon syringe filter (Corning). The details of the emulsion composition are provided in Table 5 below. Within 4 days post-preparation at room temperature, crystals were observed in the product by microscopy.

TABLE 5

| Component | Amount (g) | Concentration (w/w %) | Ratio to Aprepitant |
|---|---|---|---|
| Aprepitant | 0.250 | 0.250 | 1 |
| Lipoid E 80 | 2.50 | 2.50 | 10 |
| Soybean Oil | 15.0 | 15.0 | 60 |
| Oleic Acid | 0.125 | 0.125 | 0.5 |
| Water for Injection | 82.1 | 82.1 | 328 |
| Total | 100 | 100 | — |

Example 6: Preparing Emulsions Containing Aprepitant and Dexamethasone Sodium Phosphate for Intravenous Injection To prepare an injectable emulsion containing aprepitant and dexamethasone sodium phosphate, an oil phase was first prepared by combining 773 mg of aprepitant and 15.5 g of egg lecithin (LIPOID E 80) with 10.3 ml of ethanol. This mixture was dissolved by heating and stirring at 60° C. and 200 rpm for 15 min. To the resultant solution was added in 10.3 g of soybean oil. Heating at 60° C. and stirring at 200 rpm was continued for another 15 min. The aqueous phase was prepared by dissolving 5.77 g of sucrose and 0.515 g of sodium oleate in 71.1 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-110L, F12Y interaction chamber) at a pressure of 18,000 psi. Dexamethasone sodium phosphate (93.5 mg) dissolved in 1 ml of water for injection was mixed into the fine emulsion. This resultant fine emulsion containing both aprepitant and dexamethasone sodium phosphate was sterilized by passing it through a 0.2 μm nylon syringe filter (Corning). The details of the emulsion composition are provided in Table 6 below. By dynamic light scattering (Malvern® Zetasizer Nano ZS), the intensity-weighted particle size analyzed using NNLS fit gave a Peak 1 diameter of 95 nm. The intensity-weighted mean particle size determined using cumulant fit provided a Z-average diameter of 70 nm. The zeta potential was measured to be −43 mV by laser Doppler micro-electrophoresis (Malvern® Zetasizer Nano ZS). The pH of the injectable emulsion was 8.92. This aprepitant and dexamethasone sodium phosphate containing emulsion can be injected as is, or diluted for infusion with 5% dextrose or 0.9% saline.

TABLE 6

| Component | Amount (g) | Concentration (w/w %) | Ratio to Aprepitant |
| --- | --- | --- | --- |
| Aprepitant | 0.773 | 0.688 | 1 |
| Dexamethasone Sodium Phosphate | 0.0935 | 0.0832 | 0.121 |
| Lipoid E 80 | 15.5 | 13.8 | 20 |
| Soybean Oil | 10.3 | 9.17 | 13.3 |
| Ethanol[1] | 7.31 | 6.51 | 9.47 |
| Sucrose | 5.77 | 5.14 | 7.47 |
| Sodium Oleate | 0.515 | 0.459 | 0.667 |
| Water for Injection | 72.1 | 64.2 | 93.3 |
| Total | 112 | 100 | — |

[1]Final amount after taking into account the ethanol that was evaporated during processing.

Example 7: Stability of the Aprepitant Emulsion at Room Temperature and 5° C.

Stability of the aprepitant emulsions prepared as described in Examples 1, 2 3 and 6 was measured by incubating each emulsion preparation at room temperature (about 25° C.) or at 5° C. Mean particle size and percentage of fat globules above 5 μm were measured using DLS and light obscuration respectively to determine if they satisfy USP <729>. The emulsions were also inspected by microscopy for aprepitant crystals. Example 1 was stable at room temperature for 2 months, that is, the mean particle size and percentage of fat globules above 5 μm satisfied USP <729>. Additionally, no aprepitant crystals were visible by microscopy. After 2 months storage at room temperature, creaming was observed in Examples 1 and 6. This corresponded with the observation of aprepitant crystals. Examples 2 and 3 were stable at room temperature for 3 and 2 months respectively. After these time points, aprepitant crystals were observed in these formulations. Storage at 5° C. resulted in longer emulsion stability for Examples 1, 2, 3 and 6. Table 7 shows the characterizations of Examples 1, 2, 3 and 6 and their respective stabilities at room temperature and at 5° C.

TABLE 7

| Sample | PDI | Particle Size as Peak 1 Diameter (nm) | Particle Size as Z-Average Diameter (nm) | Zeta Potential (mV) | pH | Stability at 25° C. per USP <729> (months) | Stability at 5° C. per USP <729> |
| --- | --- | --- | --- | --- | --- | --- | --- |
| Example 1 | 0.122 | 99 | 87 | −43 | 8.74 | 2 | >10 months |
| Example 2 | 0.200 | 127 | 101 | −47 | 8.77 | 3 | >10 months |
| Example 3 | 0.219 | 88 | 68 | −42 | 8.80 | 2 | >10 months |
| Example 6 | 0.244 | 95 | 70 | −43 | 8.92 | 2 | >10 months |

Example 8: Stability of the Aprepitant Emulsion to Freeze-Thaw Cycle

Figure 1C:
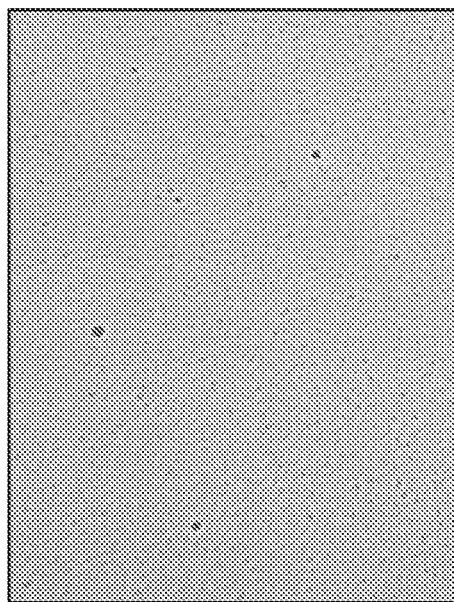
Figure 1D:
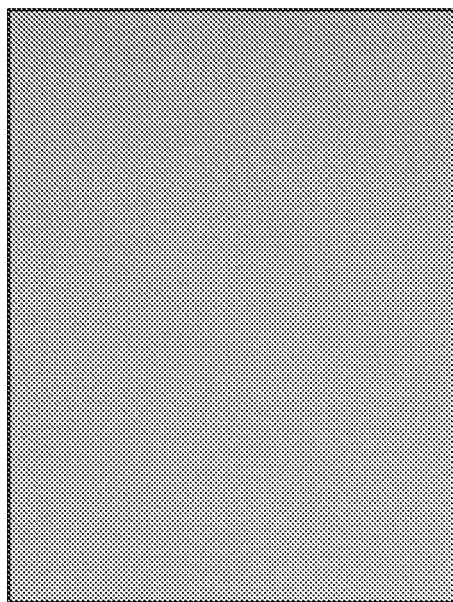

The aprepitant emulsions prepared according to Examples 1, 2, 3 and 6 were tested for stability upon exposure to a freeze-thaw cycle. Samples from the Examples 1, 2, 3 and 6 were stored at −20° C. overnight. They were thawed to room temperature the next day and visualized by microscopy. Prior to freezing, all samples did not present any visible particles under the microscope. FIG. 1 shows microscope images, at 10×, of emulsions after the freeze-thaw cycle (Examples 1, 2, 3 and 6 are shown as FIGS. 1 A, B, C, and D, respectively). Emulsions prepared as described in examples 1, 2 and 6 showed visible particles after exposure to freezing. Only Example 3 was stable after freezing. As FIG. 1C shows, no visible particles were observed for the formulation of Example 3. This enhanced stability was conferred by the presence of a large concentration of sucrose (20 w/w % in Example 3 compared to 5 w/wt % in Examples 1, 2 and 6).

Example 9: Pharmacokinetics of an Aprepitant Emulsion

Figure 2:
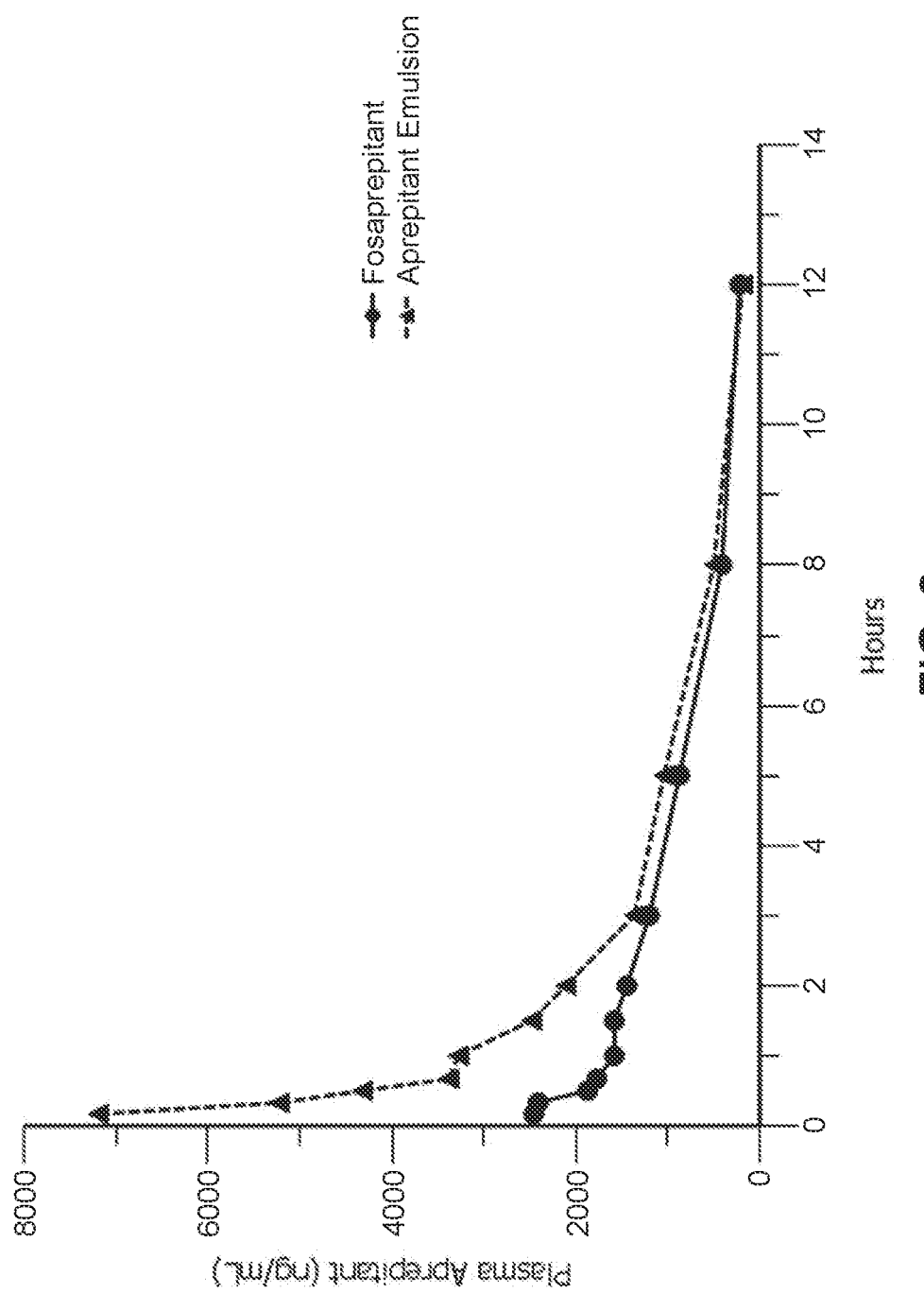
FIG. 2 shows plasma levels of aprepitant after injection of a fosaprepitant solution (●) or an aprepitant emulsion prepared as described herein (▲).

The pharmacokinetics of an aprepitant emulsion prepared according to Example 1 was determined. Two groups of six male Sprague-Dawley rats each were injected intravenously with, respectively, fosaprepitant in solution or aprepitant emulsion prepared according to Example 1. All drugs were administered at an effective concentration equivalent to 14 mg/kg aprepitant. Blood from all rats was collected at the appropriate time intervals and processed to plasma by centrifugation. Plasma samples were analyzed by LC-MS/MS for aprepitant and fosaprepitant, as appropriate. A plasma concentration versus time curve of aprepitant for the emulsion described in Example 1 and for fosaprepitant is presented in FIG. 2 (fosaprepitant in solution, ●; aprepitant emulsion, ▲). The curves indicate the initial aprepitant level reached immediately after injection of the aprepitant emulsion was almost 3 times higher than the initial aprepitant level reached immediately after injection of the fosaprepitant solution. Plasma levels of aprepitant resulting from each injection, however, were essentially the same by the 3-hour time point indicating the formulations were bioequivalent except for a delay in the conversion of fosaprepitant to aprepitant.

Example 10: Pharmacokinetics of an Aprepitant and Dexamethasone Emulsion

The pharmacokinetics of an aprepitant and dexamethasone sodium phosphate combination emulsion prepared according to Example 6 was determined. Male Sprague-Dawley rats each were injected intravenously with fosaprepitant solution (group 1), dexamethasone sodium phosphate solution (group 2), or an emulsion containing aprepitant and dexamethasone sodium phosphate prepared according to Example 6 (group 3). Groups 1 and 2 consisted of six rats each; for group 3, twelve rats were injected with the aprepitant and dexamethasone sodium phosphate combination emulsion to allow for the collection of sufficient samples for the measurement of both active ingredients.

In groups 1 and 3, a dose was administered at an effective drug concentration equivalent to 2 mg/kg aprepitant. In groups 2 and 3, a dose was administered at an effective drug concentration equivalent to 0.24 mg/kg dexamethasone sodium phosphate. Blood from all rats was collected at the appropriate time intervals and processed to plasma by centrifugation. Plasma samples were analyzed by LC-MS/MS for dexamethasone, aprepitant, and fosaprepitant, as appropriate.

Figure 3:
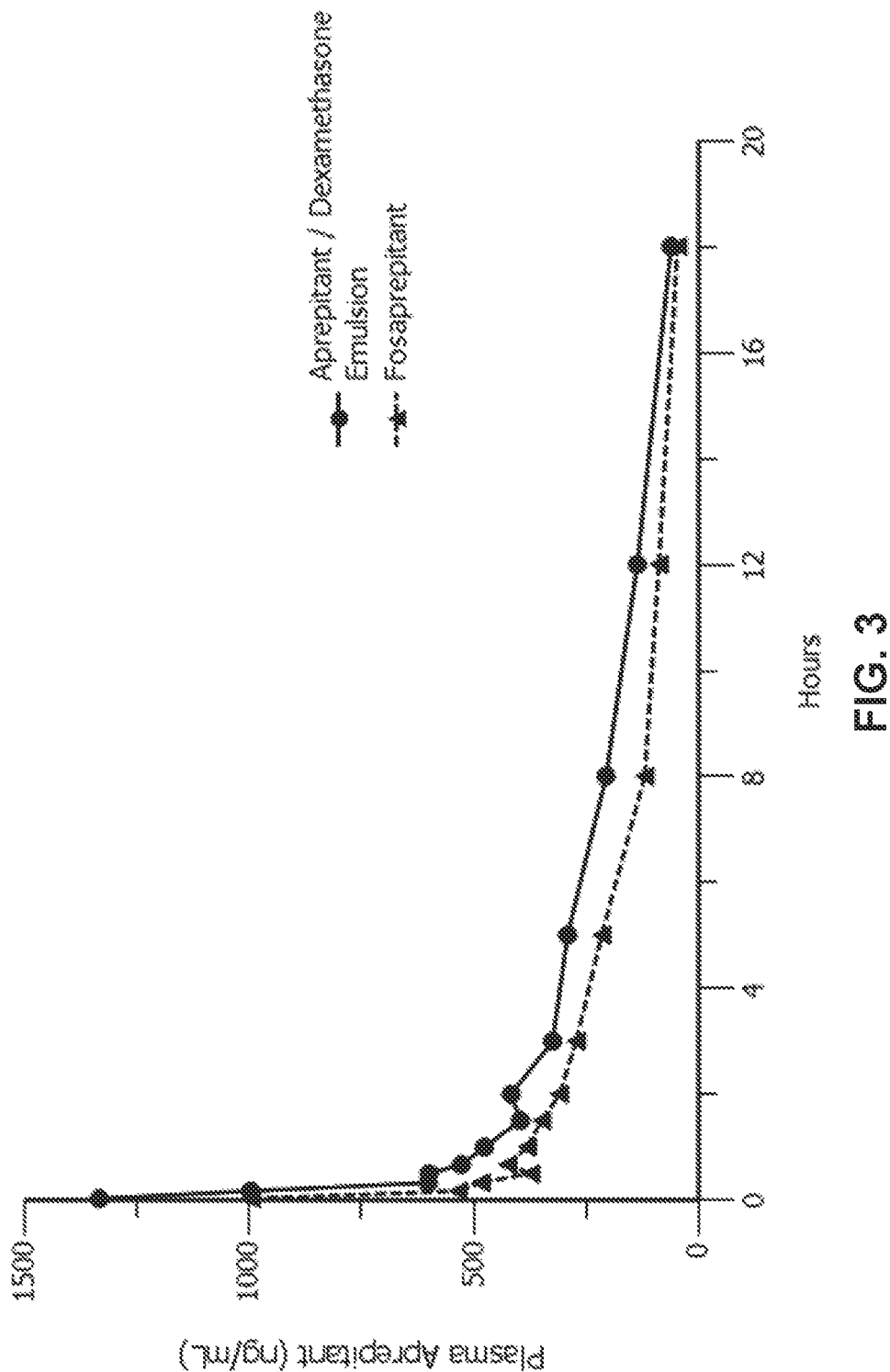
FIG. 3 shows plasma levels of aprepitant after injection of a solution of fosaprepitant (▲) or after injection of an emulsion containing aprepitant and dexamethasone prepared as described herein (●).
Figure 4:
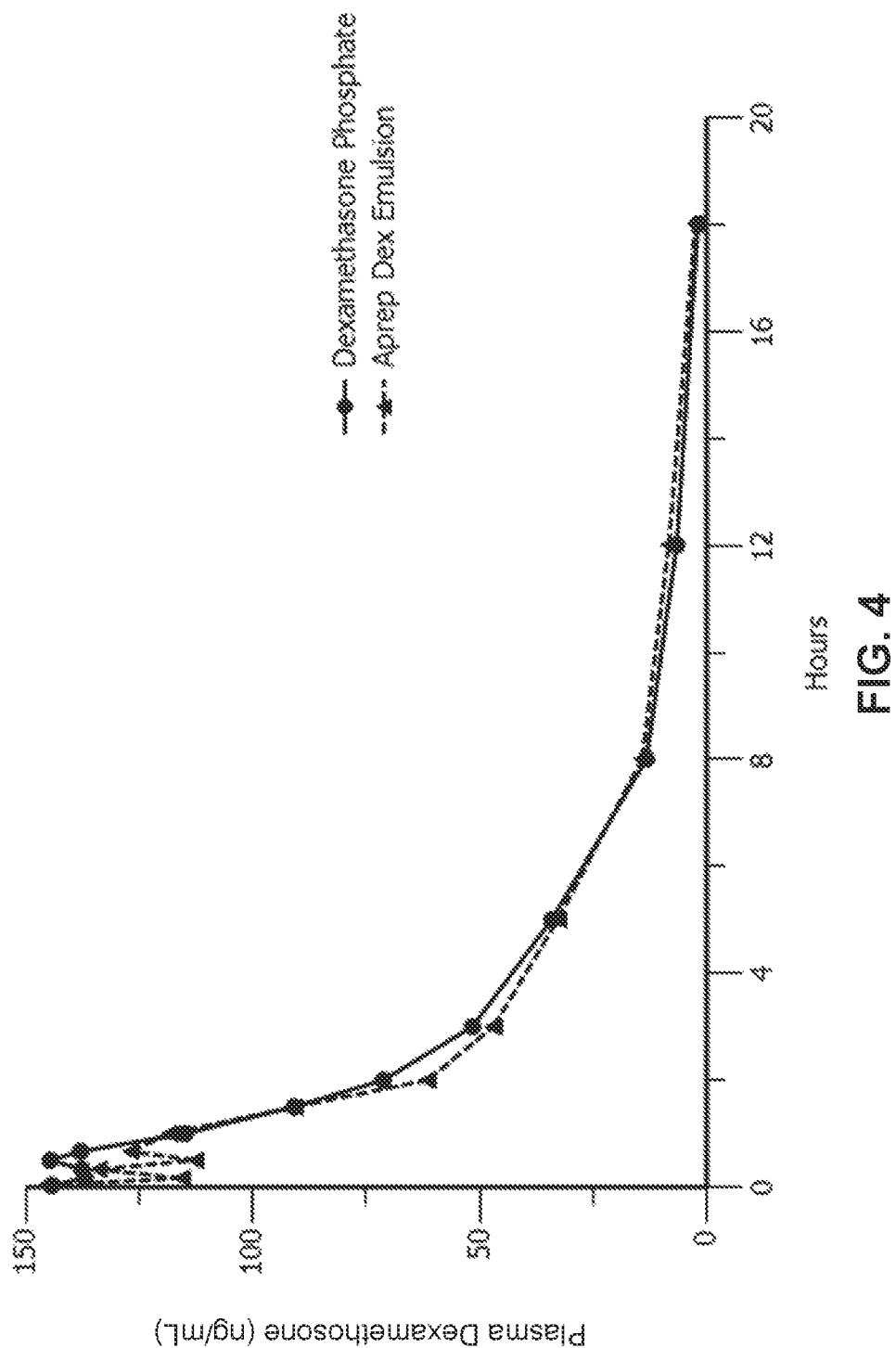
FIG. 4 shows plasma levels of dexamethasone after injection of a solution of dexamethasone sodium phosphate (●) or after injection of an emulsion containing aprepitant and dexamethasone prepared as described herein (▲).

FIGS. 3 and 4 present the plasma concentration versus time curve of aprepitant and dexamethasone, respectively. FIG. 3 compares the aprepitant plasma concentration versus time curve resulting from injection of the emulsion described in Example 6 (FIG. 3, ●) vs. injection of a solution of fosaprepitant (FIG. 3, ▲). FIG. 4 compares the dexamethasone plasma concentration versus time curve resulting from injection of a dexamethasone sodium phosphate solution (FIG. 4, ●) vs. injection of the emulsion described in Example 6. The curves indicate that the aprepitant in the emulsion is released approximately simultaneously with the dexamethasone sodium phosphate. The presence of dexamethasone sodium phosphate in the emulsion does not affect the pharmacokinetics of aprepitant.

Example 11: Preparing Aprepitant Emulsions for Intravenous Injection

To prepare the aprepitant emulsion comprising a buffering agent, an oil phase is first prepared by combining 750 mg of aprepitant, 15.0 g of egg lecithin (LIPOID E 80), 10.0 g of soybean oil and 3.75 ml of ethanol. This mixture is dissolved by heating and stirring at 70° C. and 200 rpm for 30 min. The aqueous phase is prepared by dissolving 2.17 g of sucrose and 0.500 g of sodium oleate in a mixture of 4.1 ml of 1M Tris buffer (pH 8.4) and 65.9 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 µm nylon syringe filter (Corning). Dynamic light scattering is used to determine the intensity-weighted particle size using NNLS fit to give the Peak 1 diameter, the intensity-weighted mean particle sized is determined using cumulant fit to provide the Z-average diameter. The zeta potential is measured by laser Doppler micro-electrophoresis (Malvern® Zetasizer Nano ZS). This aprepitant-containing emulsion can be injected as is, or diluted for infusion with 5% dextrose or 0.9% saline.

Example 12: Preparing Rolapitant Emulsions for Intravenous Injection

To prepare the rolapitant emulsion, an oil phase was first prepared by combining 1.080 g of rolapitant and 21.6 g of egg lecithin (LIPOID E 80) with 14.4 g of soybean oil and 5.40 ml of ethanol in a glass jar. This mixture was allowed to incubate at room temperature for 30 min followed by heating and stirring at 70° C. and 200 rpm for another 30 min. The aqueous phase was prepared by dissolving 8.06 g of sucrose and 0.720 g of sodium oleate in 100.8 ml of water for injection by heating and stirring at 35° C. and 300 rpm for 15 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was passed 8 times through a high-pressure microfluidizer (Microfluidizer® M-110P, F12Y interaction chamber) at a pressure of 20,000 psi. The outlet fine emulsion temperature was kept at approximately 25° C. using cooling water. The resultant fine emulsion was sterilized by passing through a 0.2 µm nylon filter (Nalgene). Details of the emulsion composition are provided in Table 8 below. By dynamic light scattering (Malvern® Zetasizer Nano ZS), the intensity-weighted particle size analyzed using non-negative least squares (NNLS) fit gave a Peak 1 diameter of 127 nm (Table 9). The intensity-weighted mean particle size determined using cumulant fit provided a Z-average diameter of 100 nm. The pH and osmolality of the injectable emulsion were 8.51 and 318 mmol/kg respectively. This rolapitant-containing emulsion can be injected as is, or diluted for infusion with 0.9% saline or 5% dextrose.

TABLE 8

| Component | Amount (g) | Concentration (w/w %) | Ratio to Rolapitant |
| --- | --- | --- | --- |
| Rolapitant | 1.080 | 0.728 | 1 |
| Lipoid E 80 | 21.6 | 14.55 | 20 |
| Soybean Oil | 14.4 | 9.70 | 13.3 |
| Ethanol[1] | 1.78 | 1.20 | 1.65 |
| Sucrose | 8.06 | 5.43 | 7.47 |
| Sodium Oleate | 0.720 | 0.485 | 0.667 |
| Water for Injection | 100.8 | 67.9 | 93.3 |
| Total | 148 | 100 | — |

[1]Final amount after taking into account the ethanol that was evaporated during processing.

TABLE 9

| Sample | PDI | Particle Size as Peak 1 Diameter (nm) | Particle Size as Z-Average Diameter (nm) | pH | Osmolality (mmol/kg) | Stability at 25° C. per USP <729> | Stability at 5° C. per USP <729> |
|---|---|---|---|---|---|---|---|
| Example 1 | 0.213 | 127 | 100 | 8.51 | 318 | >1 months | >1 months |

Example 13: Preparing Netupitant Emulsions for Intravenous Injection

To prepare the emulsion containing a therapeutically effective amount of netupitant, an oil phase is first prepared by combining about 750 mg of netupitant and 15.0 g of egg lecithin (LIPOID E 80) with 12.0 ml of ethanol. This mixture is dissolved by heating and stirring at 60° C. and 200 rpm for 15 min. To the resultant solution is added in 10.0 g of soybean oil. Heating at 60° C. and stirring at 200 rpm is continued for another 15 min. The aqueous phase is prepared by dissolving 5.60 g of sucrose and 0.500 g of sodium oleate in 70.0 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 μm nylon syringe filter (Corning). The details of the emulsion composition are provided in Table 10 below. By dynamic light scattering (Malvern® Zetasizer Nano ZS), the intensity-weighted particle size is analyzed using non-negative least squares (NNLS) fit to obtain a Peak 1 diameter of the particle. The intensity-weighted mean particle size is also determined using cumulant fit and provides a Z-average diameter. The zeta potential is measured to be −43 mV by laser Doppler micro-electrophoresis (Malvern® Zetasizer Nano ZS). The pH of the injectable emulsion is also measured and is preferably about pH 7.8 to 8.8. This NK-1 receptor antagonist-containing emulsion can be injected as is, or diluted for infusion with 5% dextrose or 0.9% saline.

TABLE 10

| Component | Amount (g) | Concentration (w/w %) | Ratio to Netupitant |
|---|---|---|---|
| Netupitant | 0.750 | 0.679 | 1 |
| Lipoid E 80 | 15.0 | 13.6 | 20 |
| Soybean Oil | 10.0 | 9.05 | 13.3 |
| Ethanol[1] | 8.59 | 7.78 | 11.5 |
| Sucrose | 5.60 | 5.07 | 7.5 |
| Sodium Oleate | 0.500 | 0.453 | 0.667 |
| Water for Injection | 70.0 | 63.4 | 93.3 |
| Total | 110 | 100 | — |

[1]Final amount after taking into account the ethanol that is evaporated during processing.

Example 14: Preparing Netupitant Emulsions for Intravenous Injection

To prepare the netupitant emulsion, an oil phase is first prepared by combining about 450 mg of netupitant and 9.00 g of egg lecithin (LIPOID E 80) with 4.0 ml of ethanol. This mixture is dissolved by heating and stirring at 60° C. and 200 rpm for 15 min. To the resultant solution is added 6.00 g of soybean oil. Heating at 60° C. and stirring at 200 rpm is continued for about another 15 min. The aqueous phase is prepared by dissolving 3.36 g of sucrose and 0.300 g of sodium oleate in 42.0 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 μm nylon syringe filter (Corning). The details of the emulsion composition are provided in Table 11 below. By dynamic light scattering (Malvern® Zetasizer Nano ZS), the intensity-weighted particle size is analyzed using NNLS fit to give a Peak 1 diameter. The intensity-weighted mean particle size is determined using cumulant fit provides a Z-average diameter. The zeta potential is measured by laser Doppler micro-electrophoresis (Malvern® Zetasizer Nano ZS). The pH of the injectable emulsion is also measured and is preferably about pH 7.8 to 8.8. This netupitant-containing emulsion can be injected as is, or diluted for infusion with 5% dextrose or 0.9% saline.

TABLE 11

| Component | Amount (g) | Concentration (w/w %) | Ratio to Netupitant |
|---|---|---|---|
| Netupitant | 0.450 | 0.714 | 1 |
| Lipoid E 80 | 9.00 | 14.3 | 20 |
| Soybean Oil | 6.00 | 9.52 | 13.3 |
| Ethanol[1] | 1.89 | 3.00 | 4.20 |
| Sucrose | 3.36 | 5.33 | 7.47 |
| Sodium Oleate | 0.300 | 0.476 | 0.667 |
| Water for Injection | 42.0 | 66.7 | 93.3 |
| Total | 63.0 | 100 | — |

[1]Final amount after taking into account the ethanol that is evaporated during processing.

Example 15: Preparing Netupitant Emulsions for Intravenous Injection

To prepare the netupitant emulsion, an oil phase is first prepared by combining 450 mg of netupitant and 9.00 g of egg lecithin (LIPOID E 80) with 6.0 ml of ethanol. This mixture is dissolved by heating and stirring at 60° C. and 200 rpm for 15 min. To the resultant solution is added in 6.00 g of soybean oil. Heating at 60° C. and stirring at 200 rpm is continued for another 15 min. The aqueous phase is prepared by dissolving 15.62 g of sucrose and 0.300 g of sodium oleate in 42.0 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 µm nylon syringe filter (Corning). The details of the emulsion composition are provided in Table 12 below. By dynamic light scattering (Malvern® Zetasizer Nano ZS), the intensity-weighted particle size is analyzed using NNLS fit gave a Peak 1 diameter. The intensity-weighted mean particle size is determined using cumulant fit provided a Z-average diameter. The zeta potential is measured by laser Doppler micro-electrophoresis (Malvern® Zetasizer Nano ZS). The pH of the injectable emulsion is also measured and is preferably about pH 7.8 to 8.8. This netupitant-containing emulsion is to be diluted with water for injection by 4-fold prior to injection.

TABLE 12

| Component | Amount (g) | Concentration (w/w %) | Ratio to Netupitant |
| --- | --- | --- | --- |
| Netupitant | 0.450 | 0.587 | 1 |
| Lipoid E 80 | 9.00 | 11.7 | 20 |
| Soybean Oil | 6.00 | 7.83 | 13.3 |
| Ethanol[1] | 3.27 | 4.26 | 7.26 |
| Sucrose | 15.6 | 20.4 | 34.7 |
| Sodium Oleate | 0.300 | 0.391 | 0.667 |
| Water for Injection | 42.0 | 54.8 | 93.3 |
| Total | 76.6 | 100 | — |

[1]Final amount after taking into account the ethanol that is evaporated during processing.

Example 16: Alternate Netupitant Emulsion Formulations for Intravenous Injection A netupitant emulsion is prepared which has less than 10% wt/wt of the phospholipid emulsifier and which is adjusted to a pH of less than 8.0. To prepare the netupitant emulsion, an oil phase is first prepared by combining 450 mg of netupitant and 6.67 g of egg lecithin (LIPOID E 80) with 7.2 ml of ethanol. This mixture is dissolved by heating and stirring at 60° C. and 200 rpm. Heating and stirring is carried out until the ethanol is evaporated and a thick residue is observed. To the resultant solution is added in 6.00 g of soybean oil and an appropriate amount of ethanol to obtain a clear oil phase upon heating at 60° C. The aqueous phase is prepared by dissolving 3.36 g of sucrose in 50.5 ml of water for injection at 60° C. The aqueous phase is then added to the oil phase and subsequently subjected to high-speed homogenization (Ultra-Turrax® IKA T25) at a speed of 20,000 rpm for 1 min to produce the crude emulsion. The pH of this crude emulsion is adjusted to 7.0 and then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 µm nylon syringe filter (Corning). The details of the emulsion composition are provided in Table 13 below. Within 4 days post preparation at room temperature, the emulsion product is analyzed for the presence of crystals by microscopy.

TABLE 13

| Component | Amount (g) | Concentration (w/w %) | Ratio to Netupitant |
| --- | --- | --- | --- |
| Netupitant | 0.450 | 0.672 | 1 |
| Lipoid E 80 | 6.67 | 9.95 | 14.8 |
| Soybean Oil | 6.00 | 8.96 | 13.3 |
| Sucrose | 3.36 | 5.02 | 7.47 |
| Water for Injection | 50.5 | 75.4 | 112 |
| Total | 67.0 | 100 | — |

Example 17: Alternate Netupitant Emulsion Formulations for Intravenous Injection A netupitant emulsion is prepared which contains oleic acid. To prepare the netupitant emulsion, an oil phase is first prepared by combining 250 mg of netupitant, 2.50 g of egg lecithin (LIPOID E 80), 15.0 g of soybean oil and 125 mg of oleic acid. Ten ml of ethanol is added to dissolve the mixture at 70° C. The ethanol is removed by pressure reduction in a 70° C. water bath to yield a clear oil phase. A preheated aqueous phase containing 82.1 ml of water for injection at 70° C. is added to the oil phase and subsequently subjected to high-speed homogenization (Ultra-Turrax® IKA T25) at a speed of 20,000 rpm for 1 min to produce the crude emulsion. This crude emulsion is passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 µm nylon syringe filter (Corning). The details of the emulsion composition are provided in Table 14 below. Within 4 days post preparation at room temperature, the emulsion product is analyzed for the presence of crystals by microscopy.

TABLE 14

| Component | Amount (g) | Concentration (w/w %) | Ratio to Netupitant |
| --- | --- | --- | --- |
| Netupitant | 0.250 | 0.250 | 1 |
| Lipoid E 80 | 2.50 | 2.50 | 10 |
| Soybean Oil | 15.0 | 15.0 | 60 |
| Oleic Acid | 0.125 | 0.125 | 0.5 |
| Water for Injection | 82.1 | 82.1 | 328 |
| Total | 100 | 100 | — |

Example 18: Preparing Emulsions Containing Netupitant and Dexamethasone Sodium Phosphate for Intravenous Injection To prepare an injectable emulsion containing netupitant and dexamethasone sodium phosphate, an oil phase are first prepared by combining 773 mg of netupitant and 15.5 g of egg lecithin (LIPOID E 80) with 10.3 ml of ethanol. This mixture is dissolved by heating and stirring at 60° C. and 200 rpm for 15 min. To the resultant solution is added in 10.3 g of soybean oil. Heating at 60° C. and stirring at 200 rpm is continued for another 15 min. The aqueous phase is prepared by dissolving 5.77 g of sucrose and 0.515 g of sodium oleate in 71.1 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. Dexamethasone sodium phosphate (93.5 mg) dissolved in 1 ml of water for injection is mixed into the fine emulsion. This resultant fine emulsion containing both netupitant and dexamethasone sodium phosphate is sterilized by passing it through a 0.2 μm nylon syringe filter (Corning). The details of the emulsion composition are provided in Table 15 below. By dynamic light scattering (Malvern® Zetasizer Nano ZS), the intensity-weighted particle size is analyzed using NNLS fit to determine a Peak 1 diameter. The intensity-weighted mean particle size is determined using cumulant fit to determine a Z-average diameter. The zeta potential is measured to be −43 mV by laser Doppler micro-electrophoresis (Malvern® Zetasizer Nano ZS). The preferred pH of the injectable emulsion is between about 8.5 and 9.5. This netupitant and dexamethasone sodium phosphate containing emulsion can be injected as is, or diluted for infusion with 5% dextrose or 0.9% saline.

TABLE 15

| Component | Amount (g) | Concentration (w/w %) | Ratio to Netupitant |
|---|---|---|---|
| Netupitant | 0.773 | 0.688 | 1 |
| Dexamethasone Sodium Phosphate | 0.0935 | 0.0832 | 0.121 |
| Lipoid E 80 | 15.5 | 13.8 | 20 |
| Soybean Oil | 10.3 | 9.17 | 13.3 |
| Ethanol[1] | 7.31 | 6.51 | 9.47 |
| Sucrose | 5.77 | 5.14 | 7.47 |
| Sodium Oleate | 0.515 | 0.459 | 0.667 |
| Water for Injection | 72.1 | 64.2 | 93.3 |
| Total | 112 | 100 | — |

[1]Final amount after taking into account the ethanol that is evaporated during processing.

Example 19: Preparing NK-1 Receptor Antagonist Emulsions for Intravenous Injection To prepare an NK-1 receptor antagonist emulsion comprising a buffering agent, an oil phase is first prepared by combining 750 mg of aprepitant, 15.0 g of egg lecithin (LIPOID E 80), 10.0 g of soybean oil and 3.75 ml of ethanol. This mixture is dissolved by heating and stirring at 70° C. and 200 rpm for 30 min. The aqueous phase is prepared by dissolving 2.17 g of sucrose and 0.500 g of sodium oleate in a mixture of 4.1 ml of 1M Tris buffer (pH 8.4) and 65.9 ml of water for injection. This mixture is stirred at 300 rpm at room temperature for 30 min. The aqueous phase is then added to the oil phase and subsequently subjected to high-speed homogenization (Ultra-Turrax® IKA T25) at a speed of 20,000 rpm for 1 min to produce the crude emulsion. This crude emulsion is then passed 8 times through an ice-cooled high-pressure microfluidizer (Microfluidizer® M-110L, F12Y interaction chamber) at a pressure of 18,000 psi. The resultant fine emulsion is sterilized by passing it through a 0.2 μm nylon syringe filter (Corning). Dynamic light scattering is used to determine the intensity-weighted particle size using NNLS fit to give the Peak 1 diameter, the intensity-weighted mean particle sized is determined using cumulant fit to provide the Z-average diameter. The zeta potential is measured by laser Doppler micro-electrophoresis (Malvern® Zetasizer Nano ZS). This aprepitant-containing emulsion can be injected as is, or diluted for infusion with 5% dextrose or 0.9% saline.

Example 20: Stability of the Rolapitant Emulsion at Room Temperature and 5° C.

Stability of the rolapitant emulsion prepared as described in Example 12 was measured by incubating the emulsion preparation at room temperature (about 25° C.) or at 5° C. Mean particle size and percentage of fat globules above 5 μm were measured using DLS and light obscuration respectively and demonstrated to satisfy USP <729> after 2 months of storage. The emulsions were also inspected by microscopy for rolapitant crystals and visually for the presence of emulsion creaming. The absence of crystals or emulsion creaming further indicated product stability.

Example 21: Stability of the Netupitant Emulsion at Room Temperature and 5° C.

Stability of the netupitant emulsions prepared as described in Examples 13-17 can be measured by incubating each emulsion preparation at room temperature (about 25° C.) or at 5° C. Mean particle size and percentage of fat globules above 5 μm are measured using DLS and light obscuration respectively to determine if they satisfy USP <729>. The emulsions are also inspected by microscopy for netupitant crystals and/or visually for the presence of emulsion creaming. The absence of crystals or emulsion creaming indicates product stability.

Example 22: Stability of the Netupitant Emulsion to Freeze-Thaw Cycle

The netupitant emulsions prepared according to Examples 13-17 can be tested for stability upon exposure to a freeze-thaw cycle. Samples from the Examples 13-17 are stored at −20° C. overnight. The absence of visible particles when the samples are viewed under a microscope indicates product stability.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for preventing post-operative nausea and vomiting in a subject, comprising:
    administering an injectable pharmaceutical emulsion comprising:
        a neurokinin-1 (NK-1) receptor antagonist;
        an emulsifier;
        an oil;
        a co-surfactant; and
        an aqueous phase,
    wherein the ratio of the emulsifier to the NK-1 receptor antagonist ranges from about 18:1 to 22:1 (wt/wt %).

2. The method according to claim 1, wherein the ratio of the oil to the NK-1 receptor antagonist ranges from about 5:1 to 15:1 (wt/wt %).

3. The method according to claim 1, wherein the ratio of the oil to the NK-1 receptor antagonist ranges from about 10:1 to 15:1 (wt/wt %).

4. The method according to claim 1, wherein the emulsion comprises between about 11 wt/wt % to 15 wt/wt % of an emulsifier.

5. The method according to claim 1, wherein the emulsifier is a phospholipid.

6. The method according to claim 1, wherein the emulsion further comprises dexamethasone sodium phosphate, wherein the dexamethasone sodium phosphate is present in the aqueous phase.

7. The method according to claim 1, wherein the NK-1 receptor antagonist is selected from the group consisting of aprepitant, rolapitant, netupitant, ezlopitant, vestipitant, serlopitant, maropitant, casopitant, befetupitant, and orvepitant.

8. The method according to claim 1, wherein the pH modifier is oleic acid or a salt thereof.

9. The method according to claim 1, wherein the pH modifier is a buffer.

10. The method according to claim 9, wherein the buffer is Tris buffer.

11. The method according to claim 1, wherein the oil is soybean oil.

12. The method according to claim 1, wherein the alcohol is ethanol.

13. The method according to claim 12, wherein the ethanol is present in the emulsion at less than 10 wt/wt %.

14. The method according to claim 1, wherein the NK-1 receptor antagonist is aprepitant.

* * * * *